United States Patent
Wei et al.

(10) Patent No.: US 9,265,437 B2
(45) Date of Patent: *Feb. 23, 2016

(54) TWA MEASURING ELECTROCARDIOGRAPH, TWA MEASURING METHOD, AND TWA MEASUREMENT SYSTEM

(75) Inventors: Daming Wei, Funabashi (JP); Jiro Suto, Tokyo (JP); Takashi Kaiami, Tokyo (JP)

(73) Assignees: Wei Daming, Chiba (JP); NIHON KOHDEN CORPORATION, Tokyo (JP)

( * ) Notice: Subject to any disclaimer, the term of this patent is extended or adjusted under 35 U.S.C. 154(b) by 949 days.

This patent is subject to a terminal disclaimer.

(21) Appl. No.: 13/434,008

(22) Filed: Mar. 29, 2012

(65) Prior Publication Data

US 2012/0253213 A1    Oct. 4, 2012

(30) Foreign Application Priority Data

Mar. 29, 2011 (JP) ................. 2011-073093

(51) Int. Cl.
*A61B 5/0402* (2006.01)
*A61B 5/0452* (2006.01)
*A61B 5/04* (2006.01)
*A61B 5/00* (2006.01)

(52) U.S. Cl.
CPC .......... *A61B 5/0452* (2013.01); *A61B 5/04011* (2013.01); *A61B 5/04028* (2013.01); *A61B 5/7257* (2013.01)

(58) Field of Classification Search
None
See application file for complete search history.

(56) References Cited

U.S. PATENT DOCUMENTS

| | | | |
|---|---|---|---|
| 5,704,365 A | 1/1998 | Albrecht et al. | |
| 5,713,367 A | 2/1998 | Arnold et al. | |
| 5,935,082 A | 8/1999 | Albrecht et al. | |
| 6,668,189 B2 | 12/2003 | Kaiser et al. | |
| 6,804,550 B1* | 10/2004 | Murray | 600/509 |
| 8,874,199 B2* | 10/2014 | Kawada et al. | 600/516 |
| 2001/0029338 A1* | 10/2001 | Krishnamachari | 600/515 |

(Continued)

FOREIGN PATENT DOCUMENTS

| | | |
|---|---|---|
| JP | 2005-525899 A | 9/2005 |
| JP | 2007-517633 A | 7/2007 |

(Continued)

OTHER PUBLICATIONS

Horan et al. The Interchangeability of Vectorcardiographic Systems, American Heart Journal, Sep. 1965, vol. 70 Issue 3, pp. 365-376.*

(Continued)

*Primary Examiner* — Brian T Gedeon
(74) *Attorney, Agent, or Firm* — Sughrue Mion, PLLC

(57) ABSTRACT

A TWA measuring electrocardiograph includes: a transformation coefficient storing section configured to store a transformation coefficient for deriving a Frank's vector electrocardiogram; an electrocardiograph controlling section configured to produce a scalar electrocardiogram from electrocardiographic signals of measurement electrodes adapted to be attached to a subject, and configured to derive the Frank's vector electrocardiogram from the scalar electrocardiogram by using the transformation coefficient; and a TWA measuring section configured to measure a presence of TWA based on the derived Frank's vector electrocardiogram.

13 Claims, 22 Drawing Sheets

(56) References Cited

U.S. PATENT DOCUMENTS

| | | | |
|---|---|---|---|
| 2002/0035334 A1* | 3/2002 | Meij et al. | 600/509 |
| 2002/0138106 A1* | 9/2002 | Christini et al. | 607/9 |
| 2003/0216655 A1 | 11/2003 | Schreck | |
| 2005/0209525 A1 | 9/2005 | Bojovic et al. | |
| 2006/0224071 A1* | 10/2006 | Stewart | 600/509 |
| 2007/0260151 A1 | 11/2007 | Clifford | |
| 2009/0076402 A1 | 3/2009 | Hoium et al. | |
| 2010/0305461 A1 | 12/2010 | Wei | |

FOREIGN PATENT DOCUMENTS

| | | | |
|---|---|---|---|
| JP | 2008-100080 A | 5/2008 | |
| JP | 2010-538802 A | 12/2010 | |

OTHER PUBLICATIONS

European Search Report dated Aug. 8, 2012 issued in corresponding European Patent Application No. 12161365.7.

Man, et al., "Individually Improved VCG Synthesis", Computers in Cardiology, Sep. 13, 2009, pp. 277-280.

Rubel, et al., "Quantitative Assessment of Eight Different Methods for Synthesizing Frank VCGs From Simultaneously Recorded Standard ECG Leads", Journal of Electrocardiology, Jan. 1, 1991, vol. 24, pp. 197-202.

Takahashi, et al., "Development of Digital Image Surface and its Application to derived 12-lead ECG", Computer Information Technology, Oct. 16, 2007, pp. 1122-1126.

Office Action dated May 5, 2014 issued by the State Intellectual Property Office of P.R. China in corresponding Chinese Application No. 201210090420.4.

S Man et al., "Individually Improved VCG Synthesis", Computers in Cardiology, Dec. 31, 2009, pp. 277-280.

Zhang Lihong et al., "A Method of Comprehensive Measurement of ECG and VCG", Huazhong University of Science and Technology, Dec. 31, 1998, 10 pgs. total.

Office Action issued Feb. 4, 2014 by the Japanese Patent Office in corresponding Japanese Application No. 2011-073093.

Office Action dated Feb. 2, 2015, issued by the State Intellectual Property Office of P.R. China in counterpart Chinese Application No. 201210090420.4.

* cited by examiner

ORIGINAL SIGNAL

CORRECTED SIGNAL

ALTERNANS VALUE (Dower): 7.39uV

TWA MEASURING ELECTROCARDIOGRAPH, TWA MEASURING METHOD, AND TWA MEASUREMENT SYSTEM

BACKGROUND OF THE INVENTION

The present invention relates to a TWA measuring electrocardiograph, TWA measuring method, and TWA measurement system which can measure the presence of TWA (T-wave alternans), and more particularly to a TWA measuring electrocardiograph, TWA measuring method, and TWA measurement system which can derive a Frank's vector electrocardiogram from a scalar electrocardiogram, and measure the presence of TWA from the Frank's vector electrocardiogram.

TWA appears at onset of illness such as QT prolongation syndrome, variant angina, acute myocardial ischemia, electrolyte abnormality, paroxysmal tachycardia, bradycardia, or pericardial fluid accumulation. TWA is a phenomenon in which the amplitude and polarity of the T wave appearing in an electrocardiogram are alternately changed, and an index effective to predict sudden cardiac death. TWA is not a phenomenon which can be always observed with the naked eye, and therefore its application in clinics is limited.

From the 1980s, consequently, techniques for enabling minute TWA (Microvolt TWA: MTWA) to be measured by a computer have been developed.

Examples of currently proposed techniques for measuring TWA are a measurement technique based on the MMA (Modified Moving Average) method of General Electric (GE) Company, and that based on the periodogram of Cambridge Heart (CH), Inc. which are disclosed in U.S. Pat. No. 6,668,189 and U.S. Pat. No. 5,935,082, respectively.

The measurement technique of GE Company is directed to a method of analyzing a time waveform in a time region, and is said to have resistance to noises. However, the technique does not have a long history as a measurement technique, and it is required to watch its clinical effect.

By contrast, the measurement technique of CH Inc. which is a technique in a frequency region has been used from the 1980s, and hence its effectiveness in clinics has been proved. Today, therefore, it is considered that the measurement technique based on the periodogram of CH Inc. is clinically more useful than that based on the MMA method of GE Company.

With respect to the measurement technique based on the periodogram of CH Inc., after its announcement, various techniques for performing new processes, such as a technique of measurement electrodes are added, and still now the added latest techniques have been used.

However, the measurement technique based on the periodogram of CH Inc. has several problems. For example, special measurement electrodes for eliminating noises must be used, and a Frank's vector electrocardiogram which is not necessarily commonly used must be acquired.

The use of special measurement electrodes, or the acquisition of a Frank's vector electrocardiogram imposes a burden on a measuring person because the placement of measurement electrodes and the like are different from those in the case where a usual 12-lead electrocardiogram is to be acquired. In the Frank's lead method, moreover, electrodes must be placed also on the back. Therefore, a burden is imposed also on the subject. When a usual measuring person uses the unaccustomed Frank's lead method, it is seemed that a larger measurement error caused by displacement of the attachment positions of electrodes may be produced as compared with standard lead which is prevalently employed.

SUMMARY

It is therefore an object of the invention to provide a TWA measuring electrocardiograph, TWA measuring method, and TWA measurement system which can derive a Frank's vector electrocardiogram from a scalar electrocardiogram such as a 12-lead electrocardiogram, and measure the presence of TWA from the Frank's vector electrocardiogram, thereby enabling the measuring person to measure the presence of TWA in the same manner as the case where the measuring person acquires a scalar electrocardiogram.

It is also an object of the invention to allow the presence of TWA to be measured from an electrocardiograph which is usually used, such as a 12-lead electrocardiograph, an exercise electrocardiograph, or a Holter electrocardiograph, by using a TWA analyzing method based on a vector electrocardiogram in which the effectiveness in clinics has been proven.

In order to achieve the object, according to the invention, there is provided a TWA measuring electrocardiograph comprising: a transformation coefficient storing section configured to store a transformation coefficient for deriving a Frank's vector electrocardiogram; an electrocardiograph controlling section configured to produce a scalar electrocardiogram from electrocardiographic signals of measurement electrodes adapted to be attached to a subject, and configured to derive the Frank's vector electrocardiogram from the scalar electrocardiogram by using the transformation coefficient; and a TWA measuring section configured to measure a presence of TWA based on the derived Frank's vector electrocardiogram.

The transformation coefficient storing section may include: a personal coefficient database configured to store a personal coefficient that is acquired from the subject and that is specific to the subject, as the transformation coefficient; and a group coefficient database configured to store, as the transformation coefficient, a group coefficient that is an average of a plurality of transformation coefficients acquired from an unspecified number of persons of a statistically effective population.

When the personal coefficient database stores the personal coefficient, the electrocardiograph controlling section may derive the Frank's vector electrocardiogram by using the personal coefficient as the transformation coefficient, and when the personal coefficient database does not store the personal coefficient, the electrocardiograph controlling section may derive the Frank's vector electrocardiogram by using the group coefficient stored in the group coefficient database as the transformation coefficient.

When the personal coefficient database does not store the personal coefficient, the electrocardiograph controlling section may cause a displaying section to display a message for prompting acquisition of the personal coefficient.

The electrocardiograph controlling section may calculate the personal coefficient from the electrocardiographic signals of the measurement electrodes, and store the calculated personal coefficient in the personal coefficient database.

The TWA measuring section may measure the presence of TWA based on a waveform of a vector magnitude which is obtained from the Frank's vector electrocardiogram.

The TWA measuring section may select a waveform which can contribute to measurement of the presence of TWA, from the waveform of the vector magnitude, and measure the presence of TWA from the selected waveform.

In the selected waveform which can contribute to the measurement of the presence of TWA, the TWA measuring section may detect an outlier, which may adversely affect the measurement of the presence of TWA, in an odd beat or an even beat, and correct a beat including the detected outlier.

According to the invention, there is also provided a TWA measuring method comprising: attaching measurement electrodes to a subject; producing a scalar electrocardiogram from electrocardiographic signals of the measurement electrodes; acquiring a transformation coefficient for deriving a Frank's vector electrocardiogram; deriving the Frank's vector electrocardiogram from the scalar electrocardiogram by using the transformation coefficient; and measuring a presence of TWA from the derived Frank's vector electrocardiogram.

The TWA measuring method may further comprise: before acquiring the transformation coefficient, attaching measurement electrodes to the subject, and producing a scalar electrocardiogram and a Frank's vector electrocardiogram; and calculating, based on the produced scalar electrocardiogram and Frank's vector electrocardiogram, the transformation coefficient.

In the process of deriving the Frank's vector electrocardiogram, when there is a personal coefficient that is acquired from the subject and that is specific to the subject, the personal coefficient may be used as the transformation coefficient, and, when there is not the personal coefficient, a group coefficient may be used as the transformation coefficient, the group coefficient being an average of a plurality of transformation coefficients acquired from an unspecified number of persons of a statistically effective population.

In the process of measuring the presence of TWA, the presence of TWA may be measured based on a waveform of a vector magnitude which is obtained from the Frank's vector electrocardiogram.

In the process of measuring the presence of TWA, a waveform which can contribute to measurement of the presence of TWA may be selected from the waveform of the vector magnitude, and the presence of TWA may be measured from the selected waveform.

In the process of measuring the presence of TWA, in the selected waveform which can contribute to the measurement of the presence of TWA, an outlier, which may adversely affect the measurement of the presence of TWA, is detected in an odd beat or an even beat, and a beat including the detected outlier may be corrected.

According to the invention, there is also provided a TWA measurement system comprising: the TWA measuring electrocardiograph; and an electrocardiogram management system configured to manage information related to the Frank's vector electrocardiogram derived by the TWA measuring electrocardiograph, and including a personal coefficient database configured to provide a personal coefficient as the transformation coefficient to the TWA measuring electrocardiograph.

The electrocardiograph controlling section of the TWA measuring electrocardiograph may acquire the personal coefficient, from the personal coefficient database of the TWA measuring electrocardiograph or the personal coefficient database of the electrocardiogram management system.

DETAILED DESCRIPTION OF EMBODIMENTS

Hereinafter, an embodiment of the TWA measuring electrocardiograph, TWA measuring method, and TWA measurement system of the invention will be described in detail by exemplifying the case where a 12-lead electrocardiogram is used, with reference to the drawings. Although the case where a 12-lead electrocardiogram is used will be exemplarily described in the embodiment, the invention can be applied also to the case where a scalar electrocardiogram including the derived lead is used.

In the TWA measuring electrocardiograph, TWA measuring method, and TWA measurement system of the invention, a 12-lead electrocardiogram is produced from electrocardiographic signals of measurement electrodes. The 12-lead electrocardiogram to be produced targets 12-lead electrocardiograms which are produced by any one of various measuring methods. For example, not only a usual standard 12-lead electrocardiogram, but also a derived 12-lead electrocardiogram which is derived by using a conversion matrix are targeted. Moreover, also a Holter electrocardiogram in which the lead number is two, and an exercise electrocardiogram are targeted as far as a 12-lead electrocardiogram can be produced.

In the TWA measuring electrocardiograph, TWA measuring method, and TWA measurement system of the embodiment, as described above, a Frank's vector electrocardiogram can be derived from a 12-lead electrocardiogram which is produced by any one of various measuring methods, and the presence of TWA which is effective in prognostic diagnosis of sudden cardiac death can be measured from the derived Frank's vector electrocardiogram.

In the embodiment, the term "patient" is used as a specific example of the subject. However, the subject includes not only the patient who receives a diagnosis in a hospital, but also a user of an institution other than a hospital, such as a medical examination center or clinic which performs health checkup, or a usual house.

[Configuration of TWA Measuring Electrocardiograph]

First, the configuration of the TWA measuring electrocardiograph of the embodiment will be described.

Figure 1:
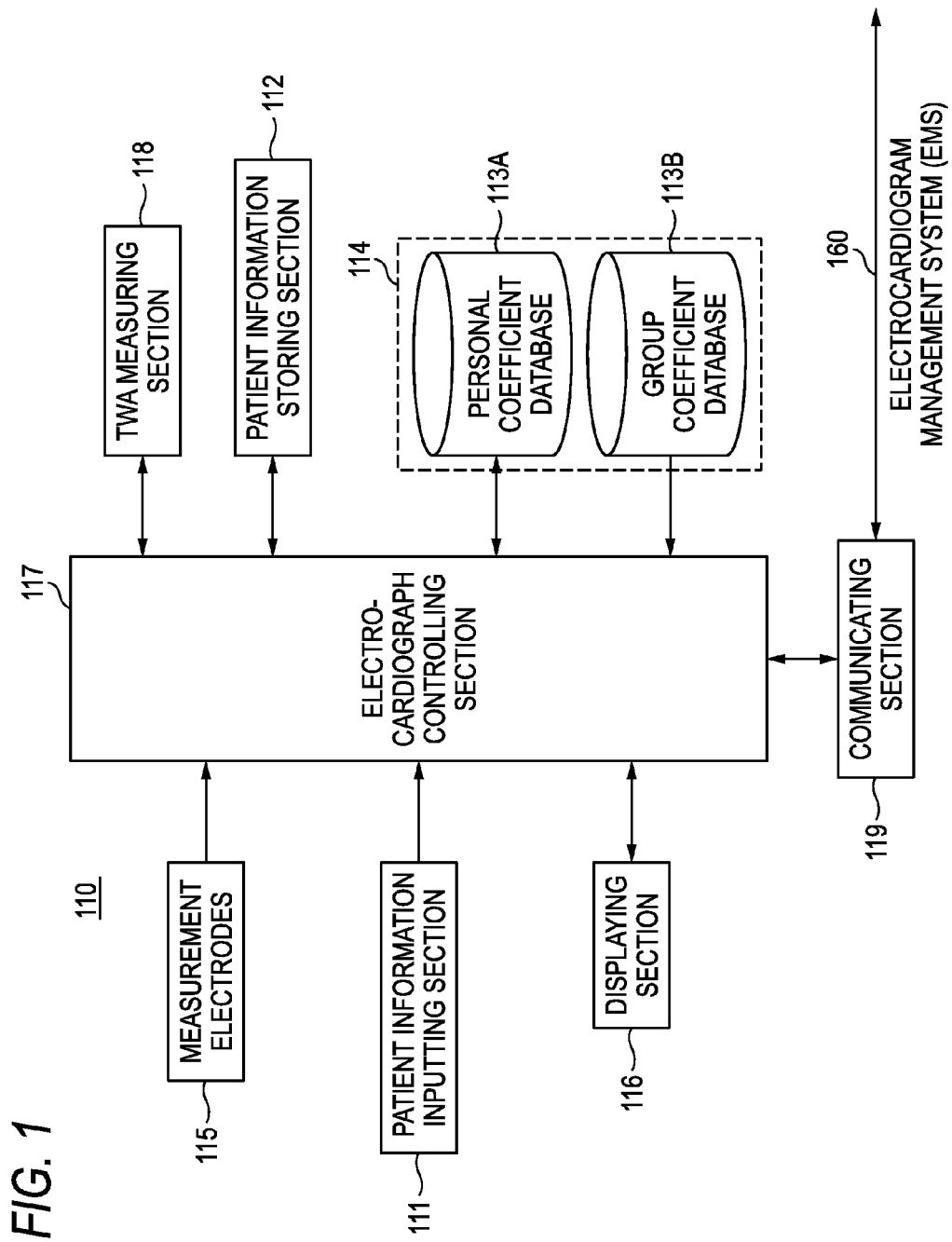
FIG. 1 is a block diagram of a TWA measuring electrocardiograph of an embodiment.

FIG. 1 is a block diagram of the TWA measuring electrocardiograph of the embodiment.

The TWA measuring electrocardiograph 110 includes a patient information inputting section 111, a patient information storing section 112, a transformation coefficient storing section 114, measurement electrodes 115, a displaying section 116, an electrocardiograph controlling section 117, a TWA measuring section 118, and a communicating section 119. The transformation coefficient storing section 114 includes a personal coefficient database 113A and a group coefficient database 113B.

The patient information inputting section 111 is used for inputting patient information by means of key operations of the measuring person. Specifically, the patient information contains a patient ID (specific ID and individual ID) (for acquiring a personal coefficient), the name of the patient (for acquiring the personal coefficient), the age of the patient (for acquiring a group coefficient), and the sex of the patient (for acquiring the group coefficient).

The patient information storing section 112 stores the patient information which is input through the patient information inputting section 111. For example, the specific ID "C123" and individual ID "A123" of the patient, the name of the patient, the age of the patient, and the sex of the patient are stored as the patient ID.

The transformation coefficient storing section 114 stores a transformation coefficient for deriving a Frank's vector electrocardiogram from the 12-lead electrocardiogram.

The personal coefficient database 113A constituting the transformation coefficient storing section 114 stores a personal coefficient which is previously acquired from a specific patient, and which is specific to the subject, as the transformation coefficient. The personal coefficient is stored for each patient and in time series. In the above-described case, for example, the specific ID "C123" of the patient, the individual ID "A123" of the patient, and the name of the patient are added as additional information of the personal coefficient, and stored for each patient and in time series.

When a Frank's vector electrocardiogram is to be derived, usually, it is sufficient to use one latest personal coefficient. Even so, a plurality of personal coefficients are stored in time series because there is a case where the progress of symptoms or the recovery state can be known by observing a change of the personal coefficient or that of a Frank's vector electrocardiogram which is produced by using past personal coefficients and the current personal coefficient.

The group coefficient database 113B constituting the transformation coefficient storing section 114 stores, as a transformation coefficient, a group coefficient which is the average of a plurality of transformation coefficients acquired from an unspecified number of persons of a statistically effective population in order to derive a Frank's vector electrocardiogram of the patient. The group coefficient is stored for each sex and age group.

The measurement electrodes 115 are electrodes which are to be attached to the body surface of the patient. The measurement electrodes 115 are used when a 12-lead electrocardiogram is to be produced, or when the personal coefficient which is specific to the patient is to be acquired. The embodiment targets 12-lead electrocardiograms which are produced by various measuring methods. Therefore, the measurement electrodes 115 are attached respectively to measurement portions of the patient which are determined in the employed measuring method.

The displaying section 116 displays the patient information which is input through the patient information inputting section 111, and a measurement result of the presence of TWA which is measured by the TWA measuring section 118, on a display device, or prints out them.

The electrocardiograph controlling section 117 produces a 12-lead electrocardiogram from electrocardiographic signals of the measurement electrodes 115, and derives a Frank's vector electrocardiogram from the 12-lead electrocardiogram by using the transformation coefficient of the transformation coefficient storing section 114. When the personal coefficient acquired from the patient exists in the personal coefficient database 113A, the electrocardiograph controlling section 117 derives a Frank's vector electrocardiogram while using the personal coefficient as the transformation coefficient. This is because, when the personal coefficient of the patient is used, the accuracy of the measurement of TWA is improved. By contrast, when the personal coefficient acquired from the patient does not exist in the personal coefficient database 113A, a Frank's vector electrocardiogram is derived while using the group coefficient existing in the group coefficient database 113B as the transformation coefficient, in order to enable the measurement of TWA to be performed even when there is no personal coefficient specific to the patient.

When there is no personal coefficient specific to the patient in the personal coefficient database 113A, the electrocardiograph controlling section 117 causes the displaying section 116 to display a message for prompting the acquisition of the personal coefficient of the patient. This is because the promotion of the acquisition of the personal coefficient contributes the improvement of the measurement accuracy. In the case where the personal coefficient specific to the patient is to be acquired, the electrocardiograph controlling section 117 calculates the personal coefficient specific to the patient from electrocardiographic signals of the measurement electrodes 115 attached to the body surface of the patient, and stores the calculated personal coefficient in the personal coefficient database 113A.

In the case where the personal coefficient specific to the patient is to be acquired, in order to produce a 12-lead electrocardiogram, first, the measurement electrodes 115 are attached respectively to measurement portions of the patient which are determined in each measuring method, and a 12-lead electrocardiogram is produced from electrocardiographic signals of the measurement electrodes 115. Next, the measurement electrodes 115 are attached respectively to measurement portions of the patient which are determined for producing a Frank's vector electrocardiogram, and a Frank's vector electrocardiogram is produced from electrocardiographic signals of the measurement electrodes 115. The measurement portions to which the measurement electrodes 115 are attached for producing a 12-lead electrocardiogram are different from those to which the measurement electrodes 115 are attached for producing a Frank's vector electrocardiogram. The production of a 12-lead electrocardiogram may be performed separately from that of a Frank's vector electrocardiogram. In the embodiment, however, the productions of the electrocardiograms are simultaneously performed in order to improve the working efficiency. The electrocardiograph controlling section 117 calculates a personal coefficient which is specific to the patient, and which is used for matching the 12-lead electrocardiogram to the Frank's vector electrocardiogram. The electrocardiograph controlling section 117 stores the calculated personal coefficient in the personal coefficient database 113A for each patient and in time series, while adding the specific ID of the patient, the individual ID of the patient, and the name of the patient to the personal coefficient as additional information of the personal coefficient.

The electrocardiograph controlling section 117 generally controls the above-described various operations, and also all operations of the TWA measuring electrocardiograph 110. The electrocardiograph controlling section 117 includes programs for realizing the all operations of the TWA measuring electrocardiograph 110. The operation of the electrocardiograph controlling section 117 will be described later in detail.

The TWA measuring section 118 measures the presence of TWA from the Frank's vector electrocardiogram which is derived by the electrocardiograph controlling section 117. The TWA measuring section 118 selects a waveform which can contribute to the measurement of the presence of TWA, from the waveform forming the Frank's vector electrocardiogram, and measures the presence of TWA from the selected waveform. This is because, when a waveform which can contribute to the measurement of the presence of TWA is selected, the accuracy of the measurement of TWA is improved. The operation of the TWA measuring section 118 will be described later in detail.

The communicating section 119 transmits the personal coefficient of the patient to an electrocardiogram management system (EMS) 140 (see FIG. 12), and conversely receives a personal coefficient of a patient which is requested by the electrocardiograph controlling section 117, from the EMS 140. The transmission/reception of a personal coefficient in the communicating section 119 can be performed through an intra-hospital network 160.

[Operation of TWA Measuring Electrocardiograph]

Next, the operation of the TWA measuring electrocardiograph of the embodiment will be described with reference to the flowchart of FIG. 2.

Figure 2:
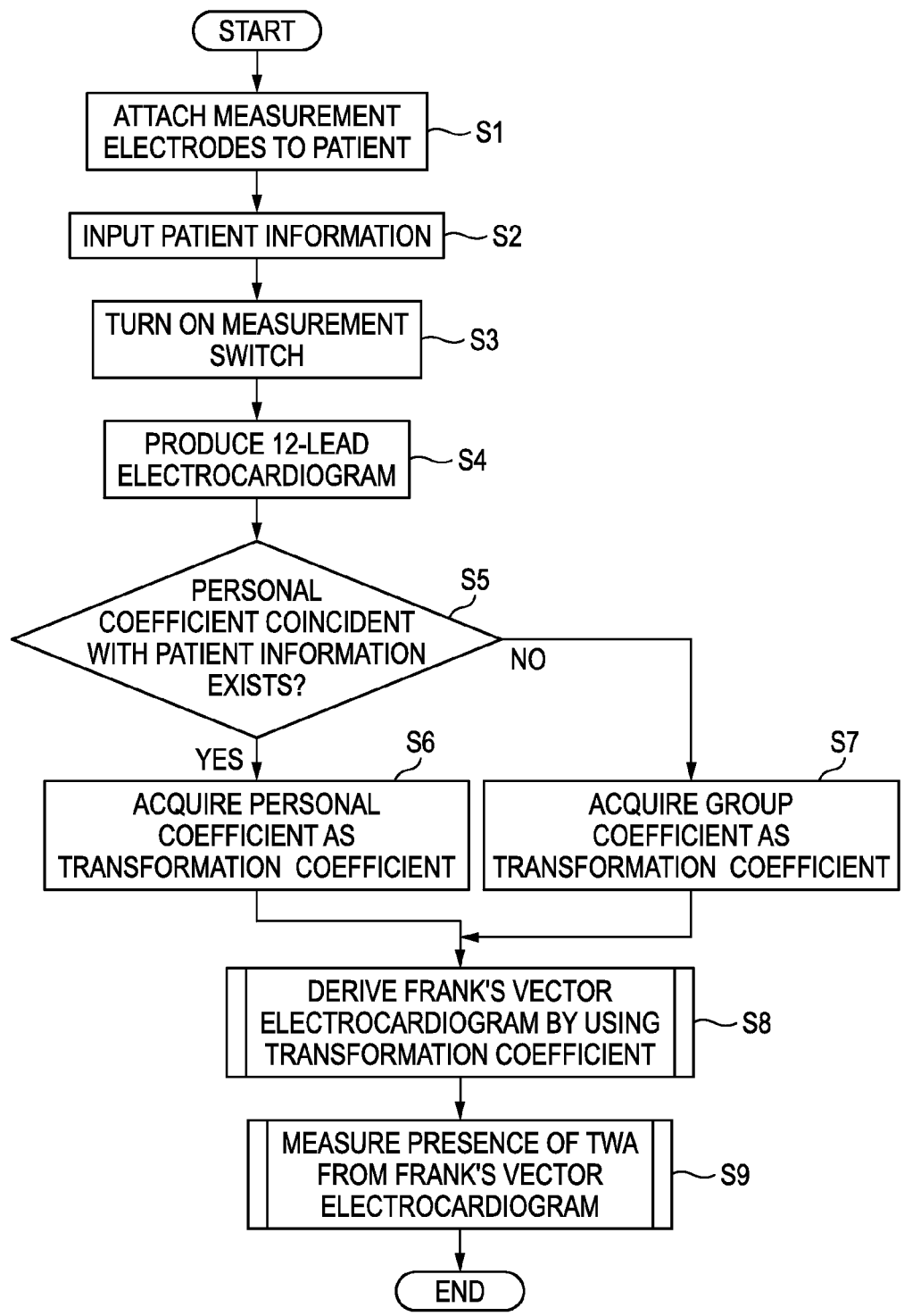
FIG. 2 is an operation flowchart of the TWA measuring electrocardiograph of the embodiment which uses a 12-lead electrocardiogram.

In the flowchart of FIG. 2, operations of steps S1 to S3 are performed by the operator (measuring person) of the TWA measuring electrocardiograph, and those of steps S4 to S8 are performed by the electrocardiograph controlling section 117. The operations of steps S1 to S8 correspond also to the procedure of the TWA measuring method of the embodiment.

Step S1

In order to produce a 12-lead electrocardiogram, the operator of the TWA measuring electrocardiograph 110 shown in FIG. 1 attaches the measurement electrodes 115 to predetermined portions of the body surface of the patient. Since the TWA measuring electrocardiograph 110 of the embodiment targets 12-lead electrocardiograms which are produced by various measuring methods, the measurement electrodes 115 are attached respectively to measurement portions of the patient which are determined in the employed measuring method. In the case where a derived 12-lead electrocardiogram of the type in which V1, V3, V4, and V6 are derived from 4 leads I, II, V2, and V5 is to be produced, for example, the measurement electrodes 115 are attached to a total of six places, i.e., four places or the right and left arms (electrodes L, R) and the right and left lower limbs (electrodes LL, RL) in order to acquire electrocardiographic signals of leads I and II, and two places or the lower left sternal edge of the fourth intercostal space, and the intersection of the left anterior axillary line with a horizontal line crossing the fifth intercostal space in order to acquire two chest leads (lead V2 and lead V5) electrocardiographic signals. In the case where a standard 12-lead electrocardiogram is to be produced, ten measurement electrodes 115 are attached to a total of ten places, i.e., six places for measuring chest leads, and four places for measuring four limb leads.

Step S2

Next, the operator inputs patient information through the patient information inputting section 111. For example, the specific ID "C123" and individual ID "A123" are input as the patient ID, and then the name of the patient, the age of the patient, and the sex of the patient are input.

Step S3

Then, the operator turns ON a measurement switch (not shown) of the TWA measuring electrocardiograph 110. When the measurement switch is turned ON, the measurement of the presence of TWA is started.

Step S4

The electrocardiograph controlling section 117 produces a 12-lead electrocardiogram from electrocardiographic signals of the six measurement electrodes 115 which are attached in step S1 to the patient.

In the case where the derived 12-lead electrocardiogram is to be produced, electrocardiographic signals of four leads, i.e., leads I and II, and two chest leads (lead V2 and lead V5) are substituted in the following formula in matrix, and the electrocardiographic signals of four leads is multiplied with a conversion matrix, thereby producing a derived electrocardiogram of the remaining four chest leads which are not actually detected by the measurement electrodes 115, i.e., lead V1, lead V3, lead V4, and lead V6 (derived lead vector).

$$\begin{vmatrix} V1 \\ V3 \\ V4 \\ V6 \end{vmatrix} = \begin{vmatrix} T1I & T1II & T12 & T15 \\ T3I & T3II & T32 & T35 \\ T4I & T4II & T42 & T45 \\ T6I & T6II & T62 & T65 \end{vmatrix} \begin{vmatrix} VI \\ VII \\ V2 \\ V5 \end{vmatrix}$$

Finally, a 12-lead electrocardiogram is produced.

In the case where the standard 12-lead electrocardiogram is to be produced, based on the electrocardiographic signals detected by the ten measurement electrodes, six limb lead waveforms (I, II, III, aVR, aVL, and aVF) of standard 12-lead, and six chest lead waveforms (V1, V2, V3, V4, V5, and V6) of standard 12-lead are calculated, and a 12-lead electrocardiogram is finally produced.

Steps S5 to S7

Next, the electrocardiograph controlling section 117 acquires the transformation coefficient for deriving a Frank's vector electrocardiogram, from the transformation coefficient storing section 114.

The electrocardiograph controlling section 117 determines whether a personal coefficient coincident with the patient information which is input in step S2 exists in the personal coefficient database 113A or not. Specifically, it is determined whether a personal coefficient coincident with the specific ID "C123" and individual ID "A123" which are input from the patient information inputting section 111 exists in the personal coefficient database 113A or not.

If a personal coefficient coincident with the patient information is in the personal coefficient database 113A, the electrocardiograph controlling section 117 acquires the personal coefficient of the patient from the personal coefficient database 113A. Personal coefficients are stored for respective patients and in time series. In the case where a plurality of personal coefficients exist for the patient, therefore, the latest personal coefficient is acquired.

By contrast, if a personal coefficient coincident with the patient information is not in the personal coefficient database 113A, the electrocardiograph controlling section 117 acquires a group coefficient coincident with the age and sex of the patient which are input as the patient information, from the group coefficient database 113B.

Step S8

The electrocardiograph controlling section 117 derives a Frank's vector electrocardiogram from the 12-lead electrocardiogram which is produced in step S4, by using a transformation coefficient which is either one of the personal coefficient specific to the patient or group coefficient that is acquired in steps S5 to S7.

The process of deriving a Frank's vector electrocardiogram will be specifically described with reference to the operation flowchart of FIG. 3.

Step S9

The TWA measuring section 118 measures the presence of TWA from the Frank's vector electrocardiogram which is derived in step S8.

The process of measuring the presence of TWA will be specifically described with reference to the operation flowchart of FIG. 5.

Figure 3:
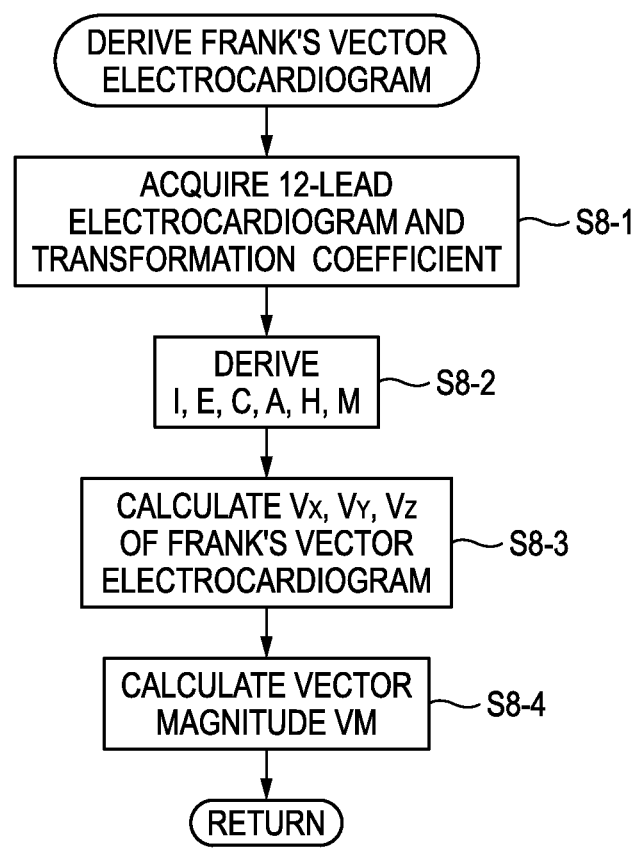
FIG. 3 is a flowchart showing procedures for deriving a Frank's vector electrocardiogram in the TWA measuring electrocardiograph of the embodiment.

The operation flowchart of FIG. 3 shows the procedure for acquiring a Frank's vector electrocardiogram. The flowchart is a subroutine flowchart of step S8 in FIG. 2.

Step S8-1

The electrocardiograph controlling section 117 acquires the 12-lead electrocardiogram which is produced in step S4, and either one of the personal coefficient acquired in step S6 or the group coefficient acquired in step S7, as the transformation coefficient.

Step S8-2

The electrocardiograph controlling section 117 multiplies the 12-lead electrocardiogram by the transformation coefficient to derive six leads I, E, C, A, H, and M of the Frank's vector electrocardiogram.

Before the multiplication of the transformation coefficient, the electrocardiograph controlling section 117 performs preprocessing for removing baseline wander of the produced 12-lead electrocardiogram, in order that the DC component of the 12-lead electrocardiogram is eliminated to align the baseline. Simultaneously, preprocessing for removing high-frequency components of the 12-lead electrocardiogram is performed in order to eliminate high-frequency noises, thereby smoothing the waveform of the 12-lead electrocardiogram.

A Frank's vector electrocardiogram can be acquired by the multiplication of the 12-lead electrocardiogram by the transformation coefficient because of the following principle.

Between a 12-lead electrocardiogram L and a Frank's vector electrocardiogram F, there is a relationship such as shown in Formula 1 below. In the formula, $\alpha$ represents a transformation coefficient.

$$L\alpha = F \qquad \text{Formula 1}$$

In Formula 1, specifically, L indicates an arrangement (n×8) of the 12-lead electrocardiogram, $\alpha$ indicates a transformation coefficient in which the personal coefficient or the group coefficient is used, and F indicates an arrangement (n×6) of the Frank's vector electrocardiogram. In the example, in the case where a 12-lead electrocardiogram is to be measured, eight electrodes are used in order to measure leads I and II, lead V1, lead V2, lead V3, lead V4, lead V5, and lead V6. Therefore, the 12-lead electrocardiogram constitutes the arrangement of (n×8).

As shown in Formula 1, in order to derive the six leads I, E, C, A, H, and M of the Frank's vector electrocardiogram from the 12-lead electrocardiogram, it is requested to multiply the 12-lead electrocardiogram by the transformation coefficient $\alpha$.

In order to derive the Frank's vector electrocardiogram from the 12-lead electrocardiogram, it is necessary to previously obtain the transformation coefficient $\alpha$. Because of this, the TWA measuring electrocardiograph 110 of the embodiment is provided with the two kinds of transformation coefficients, i.e., the personal coefficient specific to the patient, and the group coefficient which is the average of a plurality of transformation coefficients acquired from an unspecified number of persons of a statistically effective population.

When the personal coefficient specific to the patient is to be acquired, for example, the measurement electrodes 115 are attached to specific portions of the patient which are determined for producing the 12-lead electrocardiogram L (leads I and II, lead V1, lead V2, lead V3, lead V4, lead V5, and lead V6), and the 12-lead electrocardiogram is produced from the electrocardiographic signals of the measurement electrodes 115. Next, the measurement electrodes 115 are attached to specific portions of the patient which are determined for producing the Frank's vector electrocardiogram F (lead I, lead E, lead C, lead A, lead H, and lead M), and the Frank's vector electrocardiogram is produced from the electrocardiographic signals of the measurement electrodes 115. In the example, the produced 12-lead electrocardiogram L (leads I and II, lead V1, lead V2, lead V3, lead V4, lead V5, and lead V6), and the produced Frank's vector electrocardiogram F (lead I, lead E, lead C, lead A, lead H, and lead M) are substituted in following Formula 2, and the personal coefficient specific to the patient is obtained as the transformation coefficient $\alpha$. The process for acquiring the personal coefficient which is the transformation coefficient will be described specifically in detail with reference to the flowchart of FIG. 11.

$$\alpha = (L^T L)^{-1} L^T F \qquad \text{Formula 2}$$

where $L^T$ represents the transposed matrix of the 12-lead electrocardiogram L, and $(L^T L)^{-1}$ represents the inverse matrix of $(L^T L)$.

As shown in Formula 1, the electrocardiograph controlling section 117 multiplies the 12-lead electrocardiogram L by the thus obtained transformation coefficient to derive lead I, lead E, lead C, lead A, lead H, and lead M of the Frank's vector electrocardiogram F.

Step S8-3

When the Frank's vector electrocardiogram F (lead I, lead E, lead C, lead A, lead H, and lead M) is derived, the electrocardiograph controlling section 117 then substitutes the values of lead I, lead E, lead C, lead A, lead H, and lead M in following Formula 3, thereby obtaining lead $V_X$, lead $V_Y$, and lead $V_Z$ of the Frank's vector electrocardiogram.

$V_X=0.61A+0.171C-0.781I$, $V_Y=0.655F+0.345M-1.0H$, $V_Z=0.133A+0.736M-0.264I-0.374E-0.231C$.

The above formulae are denoted by Formula 3.

Step S8-4

Finally, the electrocardiograph controlling section 117 squares the values of the obtained lead $V_X$, lead $V_Y$, and lead $V_Z$, adds together the squared values, and calculates the square root of the sum of the squared values, thereby calculating the value of a vector magnitude VM.

In the above, the process which is performed when the Frank's vector electrocardiogram is to be derived has been described.

The process of the operation flowchart of FIG. 3 will be described with reference to the waveform charts of FIG. 4.

Figure 4:
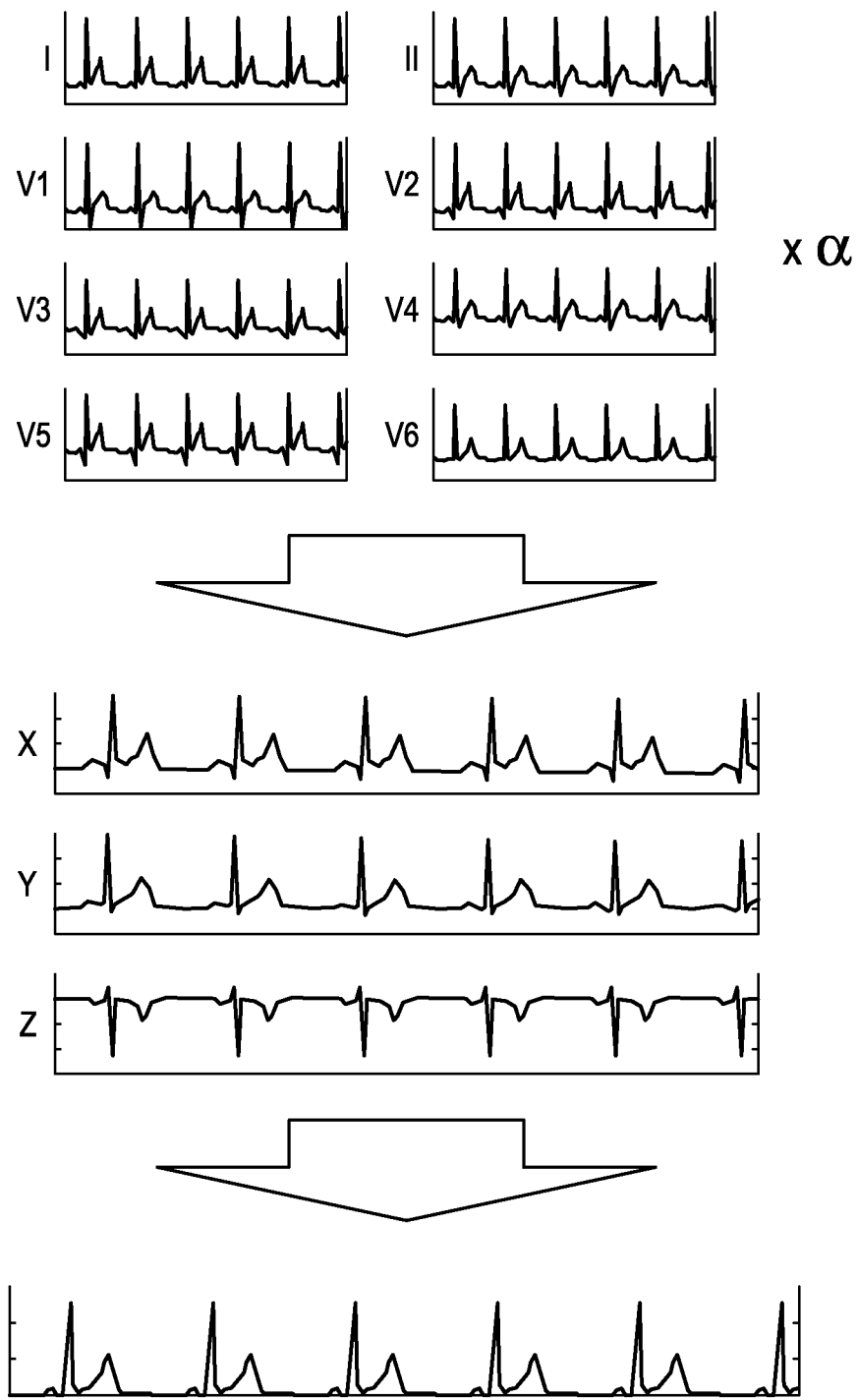
FIG. 4 is a view illustrating the process of the operation flowchart of FIG. 3, by means of waveform charts.

When eight electrocardiogram waveforms of leads I and II, lead V1, lead V2, lead V3, lead V4, lead V5, and lead V6 are obtained as the 12-lead electrocardiogram L as shown in the upper waveform charts of FIG. 4, first, the processes of removing baseline wander and high-frequency components are applied on the electrocardiogram waveforms, and the transformation coefficient α is multiplied with the resulting waveforms. Then, the values of lead I, lead E, lead C, lead A, lead H, and lead M are obtained, and electrocardiogram waveforms of lead $V_X$, lead $V_Y$, and lead $V_Z$ of the Frank's vector electrocardiogram are obtained as shown in the middle waveform charts of FIG. 4. As shown in the lower waveform chart of FIG. 4, finally, an electrocardiogram waveform of the vector magnitude VM of the Frank's vector electrocardiogram is obtained from the values of lead $V_X$, lead $V_Y$, and lead $V_Z$. The presence of TWA which is to be finally obtained will be obtained from the electrocardiogram waveform of the vector magnitude VM.

Figure 5:
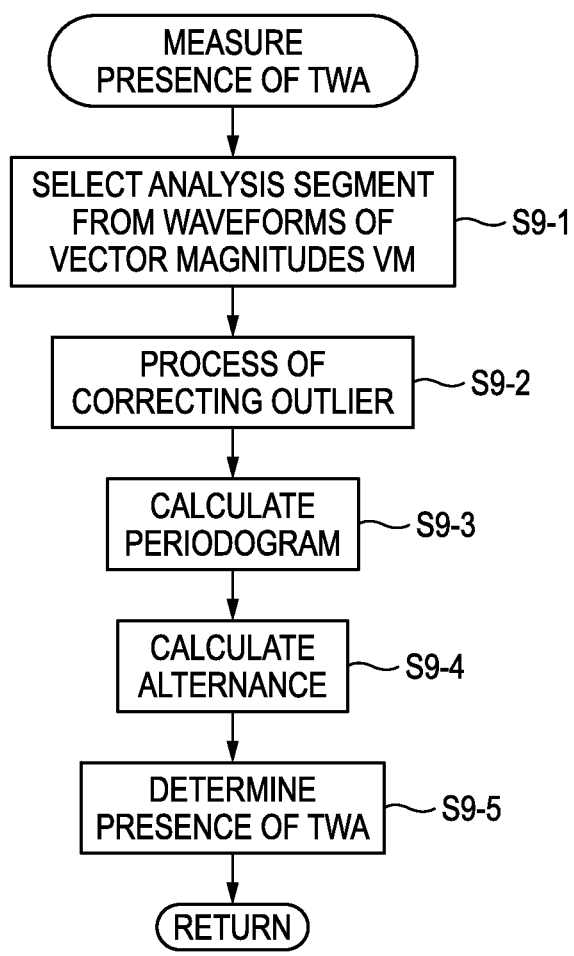
FIG. 5 is a flowchart showing procedures for measuring the presence of TWA in the TWA measuring electrocardiograph of the embodiment.

The operation flowchart of FIG. 5 shows the procedure for measuring the presence of TWA. The flowchart is a subroutine flowchart of step S9 in FIG. 2.

Step S9-1

The TWA measuring section 118 acquires the vector magnitude VM of the Frank's vector electrocardiogram which is obtained as described above, from the electrocardiograph controlling section 117. The TWA measuring section 118 selects a waveform which seems to contribute to the measurement of the presence of TWA, from the waveforms of the plural vector magnitudes VM, as described below.

The TWA measuring section 118 selects an analysis segment from the waveforms of the vector magnitudes VM. The selection of an analysis segment is performed in order to improve the accuracy of the measurement of the presence of TWA.

Figure 6:
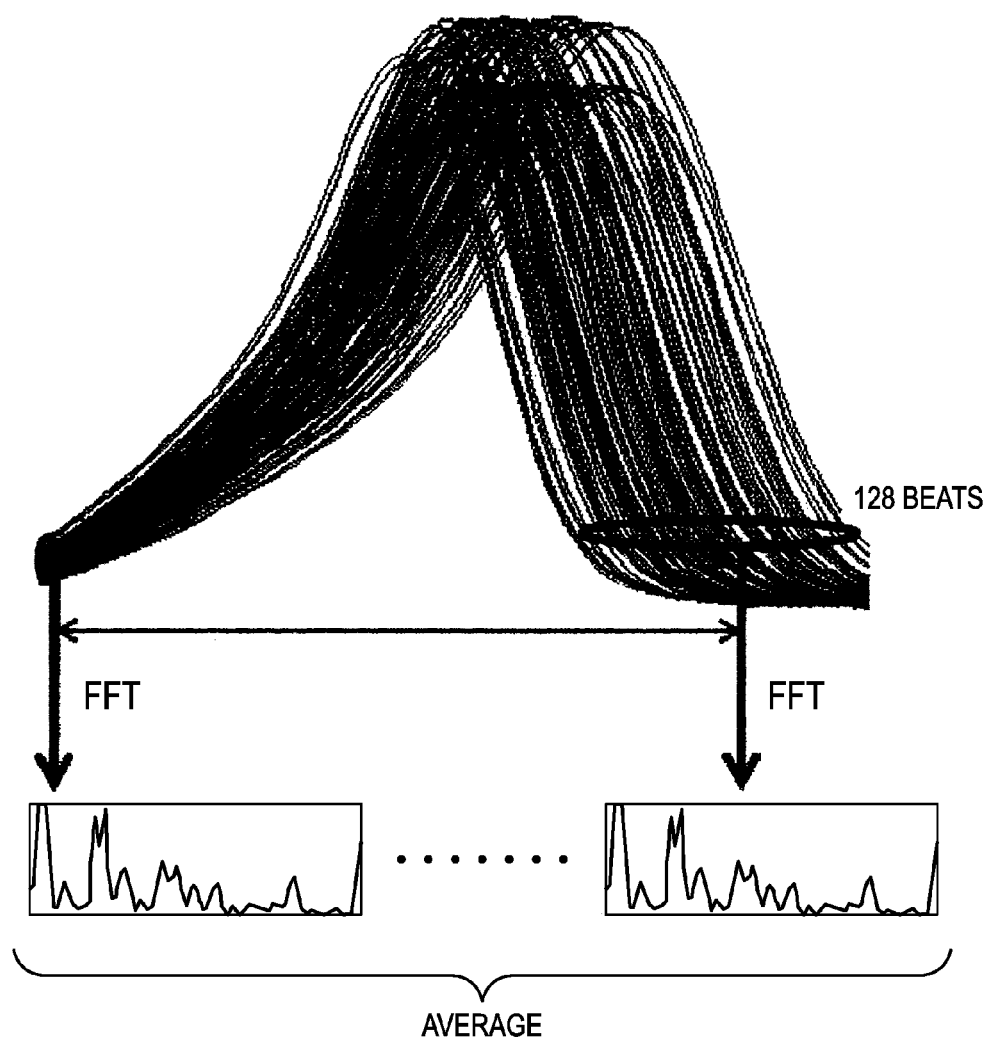
FIG. 6 is a view illustrating a process of selecting an analyzing segment.
Figure 7:
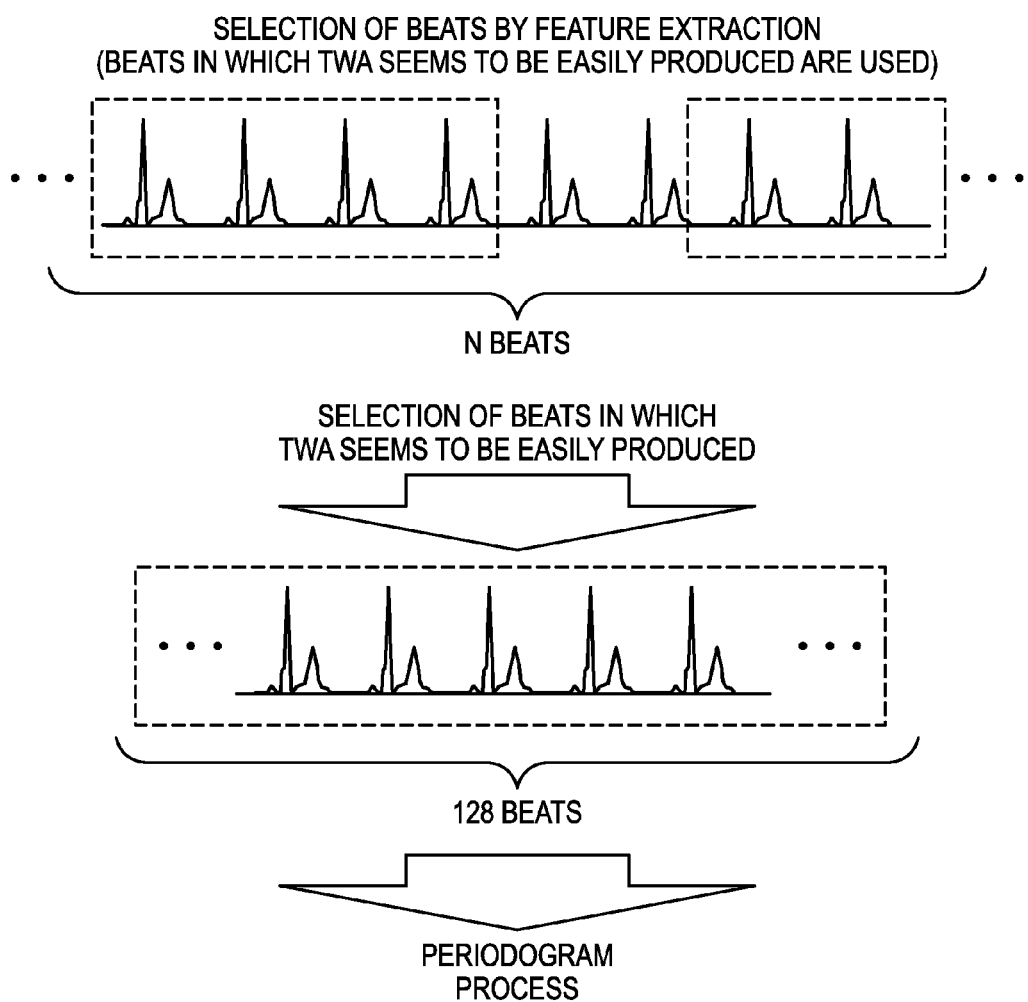
FIG. 7 is a view illustrating the process of selecting an analyzing segment.

The analysis segment is selected by, as shown in FIG. 6, selecting ST-T segments of 128 beats from the vector magnitudes VM acquired from the electrocardiograph controlling section 117. Unlike the case of FIG. 6, ST-T segments of continuous 128 beats may not be selected, but only ST-T segments of 128 beats in which TWA (TWA) seems to be easily produced may be selected from ST-T segments of N beats. In the ST-T segments of continuous 128 beats, there are beats in which many noises occur and the presence of TWA is hardly measured, and hence the measurement accuracy is affected. Therefore, 128 beats in which TWA seems to be easily produced are discontinuously selected.

Step S9-2

The TWA measuring section 118 performs a process of correcting an outlier.

Outliers which seems to adversely affect the measurement of the presence of TWA are detected while being grouped into odd and even beats, and correction is performed on the detected beats.

Specifically, the intermediate value of the electrocardiogram waveforms is obtained for odd and even beats, and the standard deviation is obtained for odd and even beats. A threshold in which the standard deviation is used as a parameter, and which is used for determining an outlier is calculated, the magnitude relationship with respect to the threshold is determined, and an outlier is determined. The value which is determined as an outlier is substituted in a correction function in which the standard deviation is used as a parameter, and a correction value is calculated. Various methods of determining such a threshold, and correction functions are known. In the embodiment, any known method or function may be used.

Figure 8:
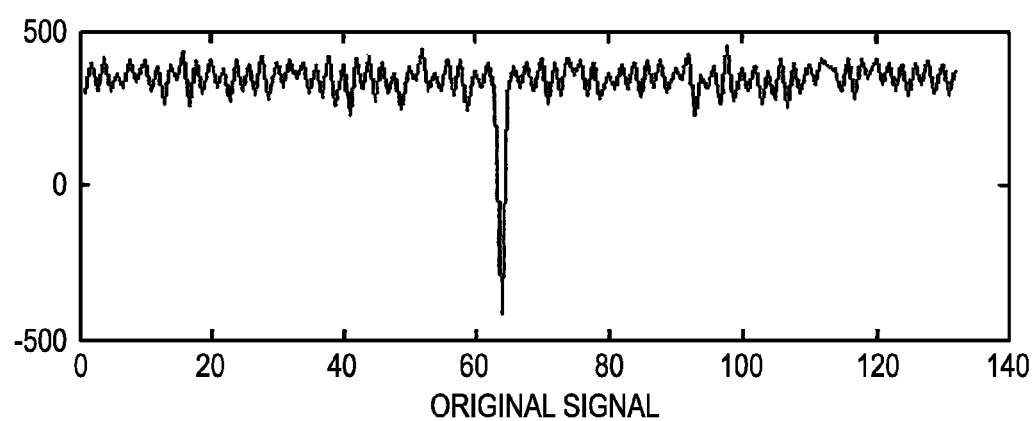
FIG. 8 shows waveform charts before and after performance of a process of correcting an outlier.
Figure 8:
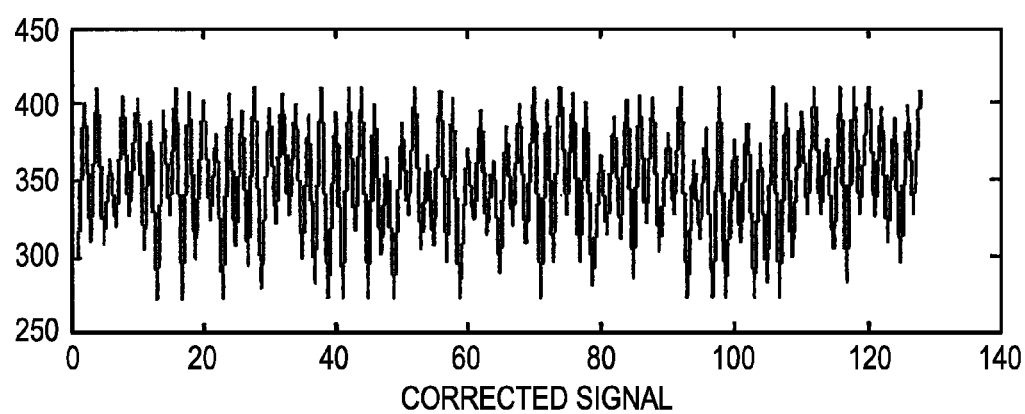

FIG. 8 shows waveform charts before and after performance of the process of correcting an outlier. In the waveform of the original signal which has not yet undergone the correcting process, as shown in the upper waveform chart of FIG. 8, a portion which largely drops in level exists in a middle portion. By contrast, in the waveform of the corrected signal which has undergone the correcting process, as shown in the lower waveform chart of FIG. 8, such a portion which largely drops in level does not exist in a middle portion. It is seen that the process of correcting an outlier achieves a significant effect.

Step S9-3

After the outlier correction, the TWA measuring section 118 performs the FFT process on the data of 128 beats, and averages the result of the process to calculate a periodogram.

Figure 9:
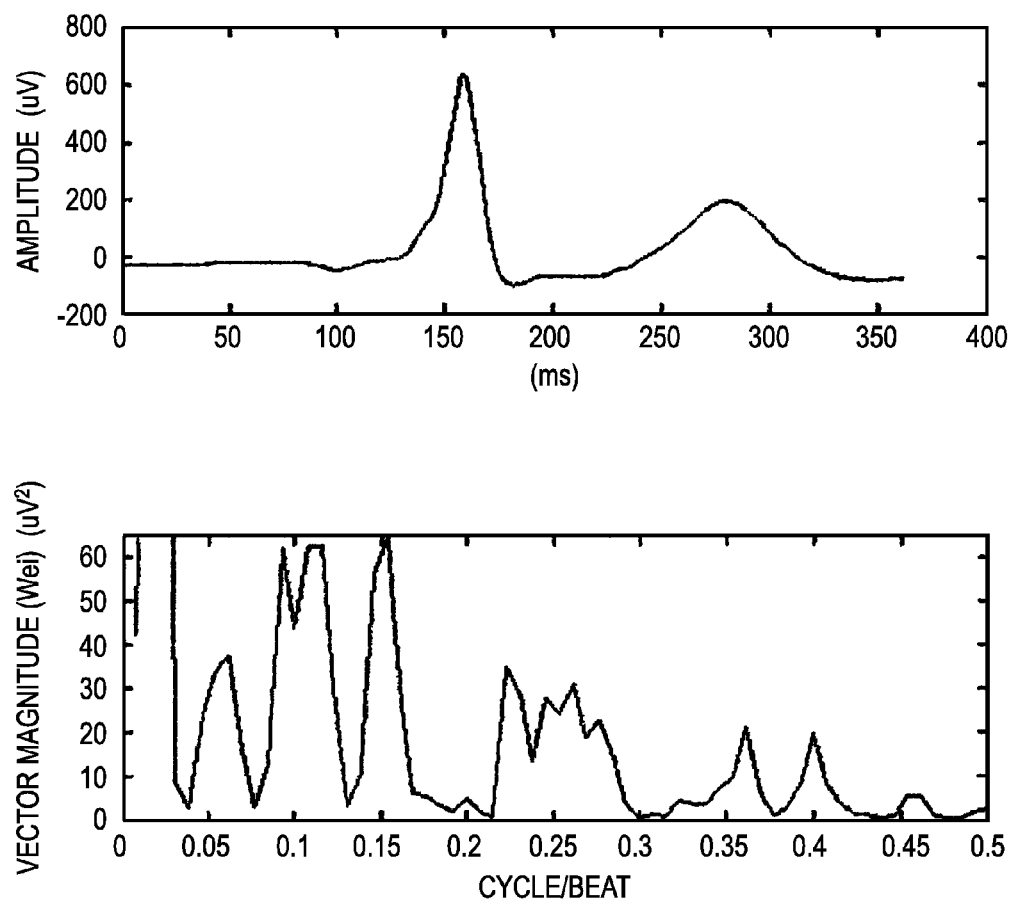
FIG. 9 is a view illustrating a process of calculating a periodogram.
Figure 10:
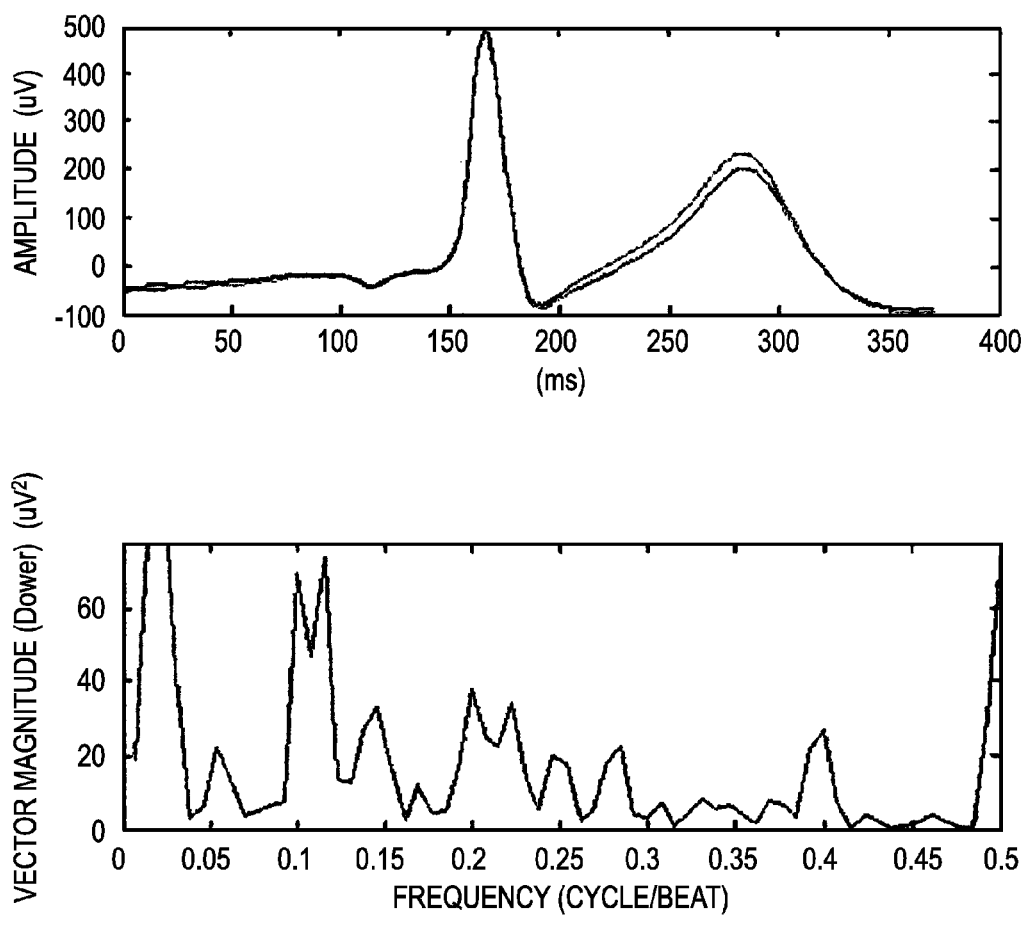
FIG. 10 is a view illustrating the process of calculating the periodogram.

FIGS. 9 and 10 are views for illustrating a periodogram. The upper waveform chars of FIGS. 9 and 10 show average waveforms of odd and even beats, respectively. The lower waveform charts of FIGS. 9 and 10 show waveforms which are obtained after a periodogram is calculated. The waveform of FIG. 9 which is obtained after a periodogram is calculated shows that, when the frequency (cycle/beat) is 0.5, the value of the vector magnitude is small. This means that there is no TWA. By contrast, the waveform of FIG. 10 which is obtained after a periodogram is calculated shows that, when the frequency (cycle/beat) is 0.5, the value of the vector magnitude is large. This means that the value of TWA is large, and the possibility that TWA exists is large.

As described above, when a periodogram is calculated, the presence of TWA can be predicted to some extent from the magnitude of the value of the vector magnitude.

Step S9-4

Next, the TWA measuring section 118 calculates alternance. In the waveform charts which are shown in FIGS. 9 and 10, and which are obtained after a periodogram is calculated, the zone where the cycle/beat frequency is from 0.44 to 0.49 is defined as a noise band, and the average $S_{NB}$ and standard deviation $\sigma_{NB}$ of the zone are obtained. The value which is obtained when the cycle/beat frequency is 0.5 is indicated by $S_{0.5}$, and the following Formula 4 is calculated, thereby calculating alternance $V_{alt}$.

$$V_{alt}=(S_{0.5}-S_{NB})^{1/2} \quad \text{Formula 4}$$

Step S9-5

The TWA measuring section 118 determines the presence of TWA. By using the standard deviation $\sigma_{NB}$ and value of alternance $V_{alt}$ which are calculated in step S9-4, the following Formula 5 is calculated, thereby calculating an alternance ratio k.

$$k=V_{alt}/\sigma_{NB} \quad \text{Formula 5}$$

Then, the presence of TWA is determined from the values of the alternance $V_{alt}$ and the alternance ratio k. Conditions for determining the presence of TWA are the alternance $V_{alt}>1.9$ μV and the alternance ratio k>3. When the determination conditions are satisfied, it is determined that TWA exists.

As described above, when the waveform of a Frank's vector electrocardiogram obtained from a 12-lead electrocardiogram is analyzed, it is possible to determine the presence of TWA in which T waves having different shapes appear alternately at each beat (ABABAB . . . ).

Figure 11:
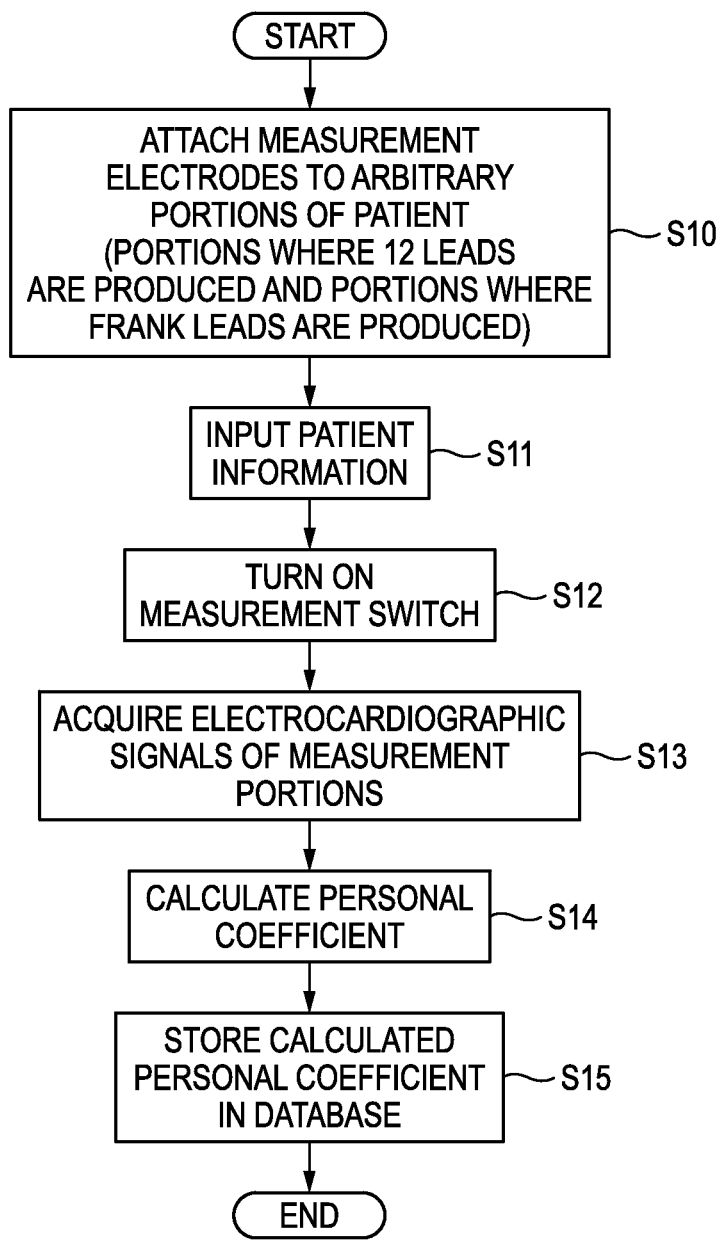
FIG. 11 is an operation flowchart of the TWA measuring electrocardiograph of the embodiment.

In the case where the personal coefficient of the patient is not stored, next, the TWA measuring electrocardiograph 110 of the embodiment causes the displaying section 116 to display the message for prompting the acquisition of the personal coefficient. At this time, the operator of the TWA measuring electrocardiograph 110 acquires the personal coefficient of the patient, and stores it in the personal coefficient database 113A of the TWA measuring electrocardiograph 110. The procedure of this case will be described in detail with reference to the operation flowchart of FIG. 11. In the flowchart of FIG. 11, the operations of steps S10 to S12 are performed by the operator of the TWA measuring electrocardiograph 110, and those of steps S13 to S15 are performed by the electrocardiograph controlling section 117. The operations of steps S13 to S15 correspond to the procedure of the TWA measuring method of the embodiment.

Step S10

In order to acquire a 12-lead electrocardiogram and a Frank's vector electrocardiogram, first, the operator attaches the measurement electrodes to specific portions of the patient.

Specifically, the measurement electrodes 115 are attached to specific portions of the patient which are determined so as to produce a 12-lead electrocardiogram (leads I and II, lead V1, lead V2, lead V3, lead V4, lead V5, and lead V6), and attached to specific portions of the patient which are determined so as to produce a Frank's vector electrocardiogram (lead I, lead E, lead C, lead A, lead H, and lead M).

Step S11

Next, the operator inputs the patient information through the patient information inputting section 111. For example, the specific ID "C123" and the individual ID "A123" are input as the patient ID, and then the name and age of the patient are input.

Step S12

Then, the operator turns ON the measurement switch (not shown) of the TWA measuring electrocardiograph 110.

Step S13

The electrocardiograph controlling section 117 acquires electrocardiographic signals of the measurement portions from the measurement electrodes 115 attached to the patient.

Step S14

The electrocardiograph controlling section 117 produces a 12-lead electrocardiogram from the electrocardiographic signals of the measurement electrodes 115, and also a Frank's vector electrocardiogram from the electrocardiographic signals of the measurement electrodes 115. In the above example, the produced 12-lead electrocardiogram (leads I and II, lead V1, lead V2, lead V3, lead V4, lead V5, and lead V6), and the produced Frank's vector electrocardiogram (lead I, lead E, lead C, lead A, lead H, and lead M) are substituted in following Formula 6, and the personal coefficient specific to the patient is calculated as the transformation coefficient α.

$$\alpha=(L^TL)^{-1}L^TF \quad \text{Formula 6}$$

where $L^T$ represents the transposed matrix of the 12-lead electrocardiogram L, and $(L^TL)^{-1}$ represents the inverse matrix of $(L^TL)$.

Step S15

The electrocardiograph controlling section 117 stores the calculated personal coefficient in the personal coefficient database 113A. When the personal coefficient is to be stored, the specific ID "C123" of the patient, the individual ID "A123" of the patient, and the name and age of the patient are added as additional information of the personal coefficient, and stored in time series.

In the above, the operations of the TWA measuring electrocardiograph and TWA measuring method of the embodiment have been described.

[Configuration of TWA Measurement System]

Next, the configuration of the TWA measurement system of the embodiment will be described.

Figure 12:
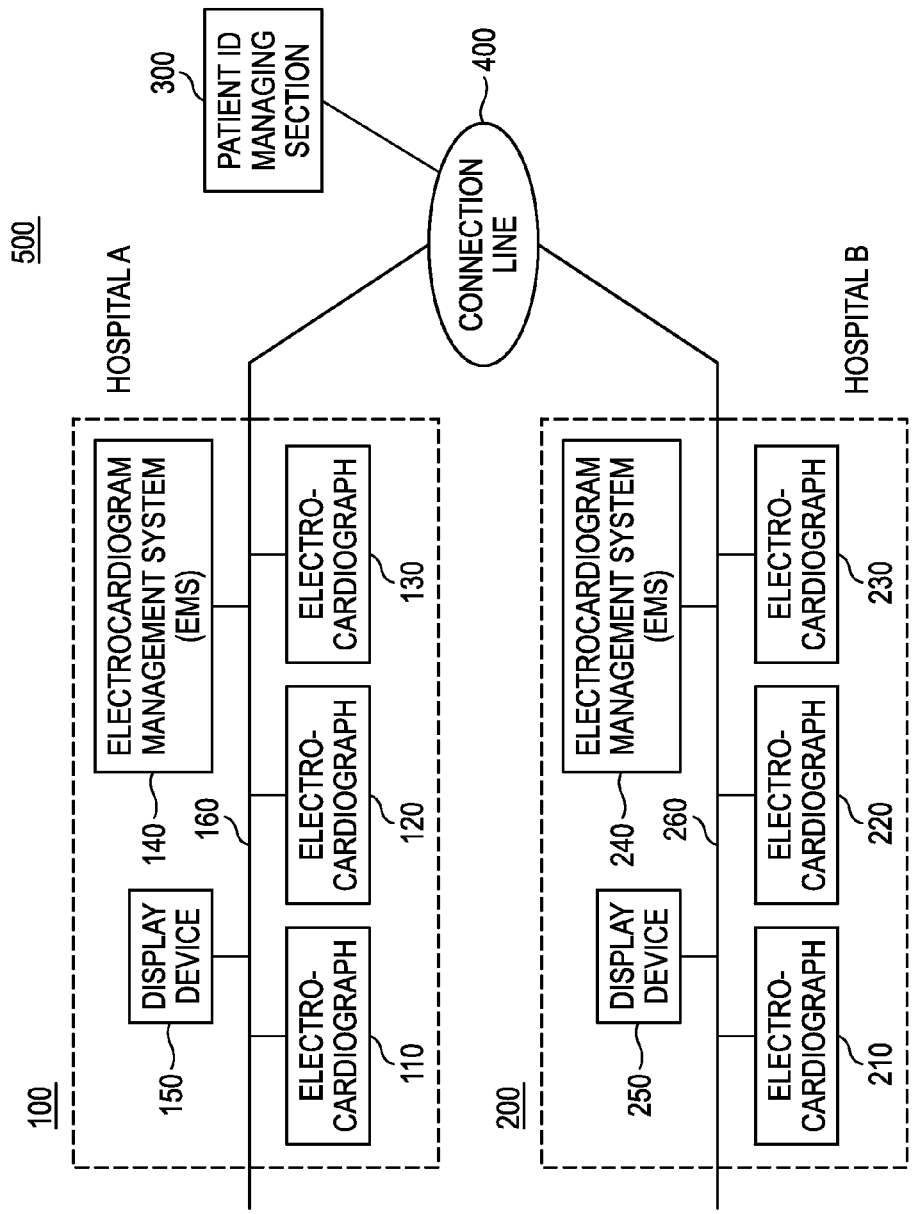
FIG. 12 is a block diagram of a TWA measurement system of the embodiment.

FIG. 12 is a block diagram of the TWA measurement system of the embodiment.

The TWA measurement system 500 has: an electrocardiogram management apparatus 100 provided in a hospital A; an electrocardiogram management apparatus 200 provided in a hospital B; a patient ID managing section 300 which manages patient IDs (specific IDs and individual IDs) in the hospitals A and B; and a connection line 400. The electrocardiogram management apparatuses 100, 200 and the patient ID managing section 300 are connected to one another through the connection line 400.

In the embodiment, the case where the electrocardiogram management apparatuses 100, 200 are provided in hospitals will be exemplified. The institutions in which the electrocardiogram management apparatuses 100, 200 are provided are not limited to hospitals. For example, they may be provided in institutions other than hospitals, such as a medical examination center, a clinic, a school, and a senior care facility which perform health checkup. Although the patient ID managing section 300 is disposed outside the electrocardiogram management apparatuses 100, 200, the section may be disposed in, for example, the electrocardiogram management apparatus 100 of the hospital A. The connection line 400 may be a dedicated line through which the electrocardiogram management apparatuses 100, 200 are connected to the patient ID managing section 300, or a wired or wireless Internet line in which security measures are taken.

The electrocardiogram management apparatus 100 of the hospital A includes TWA measuring electrocardiographs 110, 120, 130, an electrocardiogram management system (EMS) 140, and a display device 150. The TWA measuring electrocardiographs 110, 120, 130, the electrocardiogram management system (EMS) 140, and the display device 150 are connected to one another through the intra-hospital network 160. The electrocardiogram management apparatus 200 of the hospital B includes TWA measuring electrocardiographs 210, 220, 230, an electrocardiogram management system (EMS) 240, and a display device 250. The TWA measuring electrocardiographs 210, 220, 230, the electrocardiogram management system (EMS) 240, and the display device 250 are connected to one another through an intra-hospital network 260. The intra-hospital networks 160, 260 may be dedicated lines through which the TWA measuring electrocardiographs 110, 120, 130, 210, 220, 230, and the display devices 150, 250 are connected to one another a wired or wireless intranet line, or a wired or wireless Internet line in which security measures are taken.

As described above, the TWA measuring electrocardiographs 110, 120, 130, 210, 220, 230 have the functions of searching the personal coefficient of the patient, or the group coefficient, calculating and storing the personal coefficient of the patient, and measuring the presence of TWA. Therefore, programs for accomplishing the functions are installed in the TWA measuring electrocardiographs 110, 120, 130, 210, 220, 230.

The electrocardiogram management system 140 is connected to the TWA measuring electrocardiographs 110, 120, 130 through the intra-hospital network 160. The electrocardiogram management system 140 transmits and receives information relating to the TWA measurement, such as patient information, produced electrocardiogram data, and the personal coefficient to and from the TWA measuring electrocardiographs 110, 120, 130, and manages the information. The electrocardiogram management system 240 is connected to the TWA measuring electrocardiographs 210, 220, 230 through the intra-hospital network 260. The electrocardiogram management system 240 transmits and receives information relating to the TWA measurement, such as patient information, produced electrocardiogram data, and the personal coefficient to and from the TWA measuring electrocardiographs 210, 220, 230, and manages the information.

The electrocardiogram management systems 140, 240 have functions of searching the personal coefficient of the patient which is requested by the TWA measuring electrocardiograph 110, 120, 130, 210, 220, or 230 through the connection line 400, and outputting the searched personal coefficient toward the TWA measuring electrocardiograph requesting it. Therefore, programs for accomplishing the functions are installed in the electrocardiogram management systems 140, 240.

The display device 150 receives information which is produced by the TWA measuring electrocardiographs 110, 120, 130, and which relates to the measurement of TWA of the patient, from the electrocardiogram management system 140, and displays information of the patient which is designated by the operator. Moreover, the display device displays information which is acquired by the TWA measuring electrocardiographs 110, 120, 130, and which relates to the TWA measurement. The display device 250 receives information which is produced by the TWA measuring electrocardiographs 210, 220, 230, and which relates to the measurement of TWA of the patient, from the electrocardiogram management system 240, and displays information of the patient which is designated by the operator. Moreover, the display device displays information which is acquired by the TWA measuring electrocardiographs 210, 220, 230, and which relates to the TWA measurement.

The patient ID managing section 300 has a function of, when the electrocardiogram management systems 140, 240 mutually search the personal coefficient of a specific patient, converting an individual ID which is provided to the same patient by another hospital, to an individual ID which is used in this hospital. For example, the case where, to the same patient, an individual ID "A123" is provided in the hospital A, and an individual ID "B456" is provided in the hospital B will be considered. In this case, the individual ID "A123" is converted to "B456", and the individual ID "B456" is converted to A123". In the conversion of the individual ID between the hospitals, the specific ID is used. In the world, the specific ID is the only one ID which is provided to the patient. The ID can be commonly used in all hospitals in the world, and is specific to the patient. Two or more IDs cannot be provided to the same patient. The patient ID managing section 300 has a comparison table of specific IDs and individual IDs. The comparison table is always updated in response to a request from the electrocardiogram management systems 140, 240.

Figure 13:
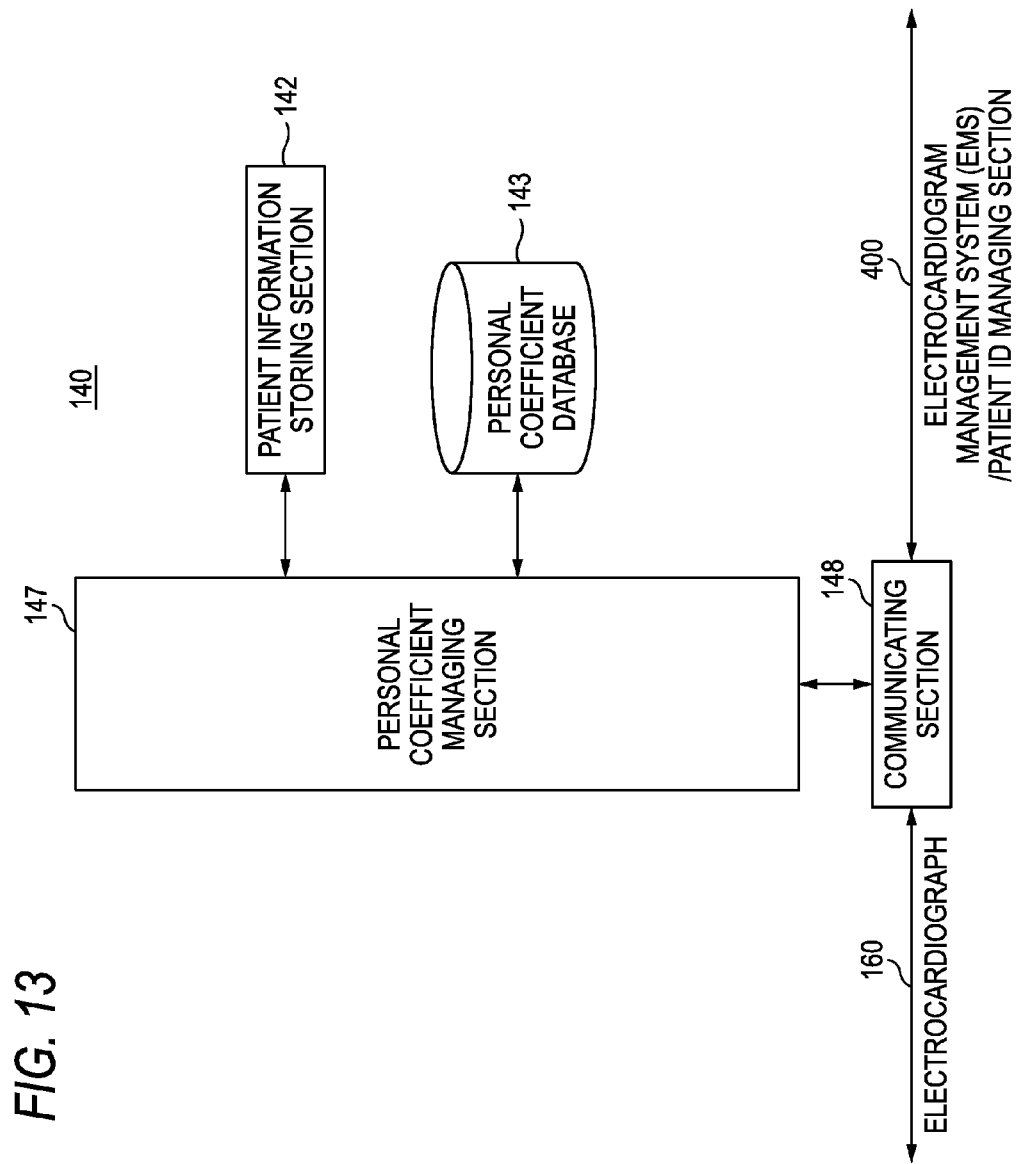
FIG. 13 is a block diagram of an electrocardiogram management system in the embodiment.

FIG. 13 is a block diagram of an electrocardiogram management system in the embodiment. Hereinafter, the configuration of the electrocardiogram management system 140 will be described. The electrocardiogram management system 240 is configured in the same manner as the electrocardiogram management system 140.

The electrocardiogram management system 140 includes a patient information storing section 142, a personal coefficient database 143, a personal coefficient managing section 147, and a communicating section 148.

The patient information storing section 142 stores patient information which is identical with that stored in the patient information storing sections of the TWA measuring electrocardiographs 110, 120, 130 (in the TWA measuring electrocardiograph 110, for example, the patient information storing section 112). The patient information storing section 142 collectively stores all information stored in the TWA measuring electrocardiographs 110, 120, 130 connected to the intra-hospital network 160.

The personal coefficient database 143 stores personal coefficients which are identical with those stored in the personal coefficient databases of the TWA measuring electrocardiographs 110, 120, 130 (in the TWA measuring electrocardiograph 110, for example, the personal coefficient database 113A). The personal coefficient database 143 collectively stores all personal coefficients stored in the TWA measuring electrocardiographs 110, 120, 130 connected to the intra-hospital network 160.

The personal coefficient managing section 147 generally controls the operation of the electrocardiogram management system 140. The personal coefficient managing section 147 has functions of storing the patient information in the patient information storing section 142, and storing and fetching the personal coefficient of the patient in and from the personal coefficient database 143. The operation of the personal coefficient managing section 147 will be described in detail.

The communicating section 148 receives the patient information and the personal coefficient from the TWA measuring electrocardiographs 110, 120, 130, and transmits the personal coefficient to the TWA measuring electrocardiographs 110, 120, 130. Furthermore, the communicating section 148 transmits the patient ID to the patient ID managing section 300, and receives the converted patient ID. The transmission and reception of the patient information and the personal coefficient are performed through the intra-hospital network 160, and those of the patient ID are performed through the connection line 400.

Figure 14:
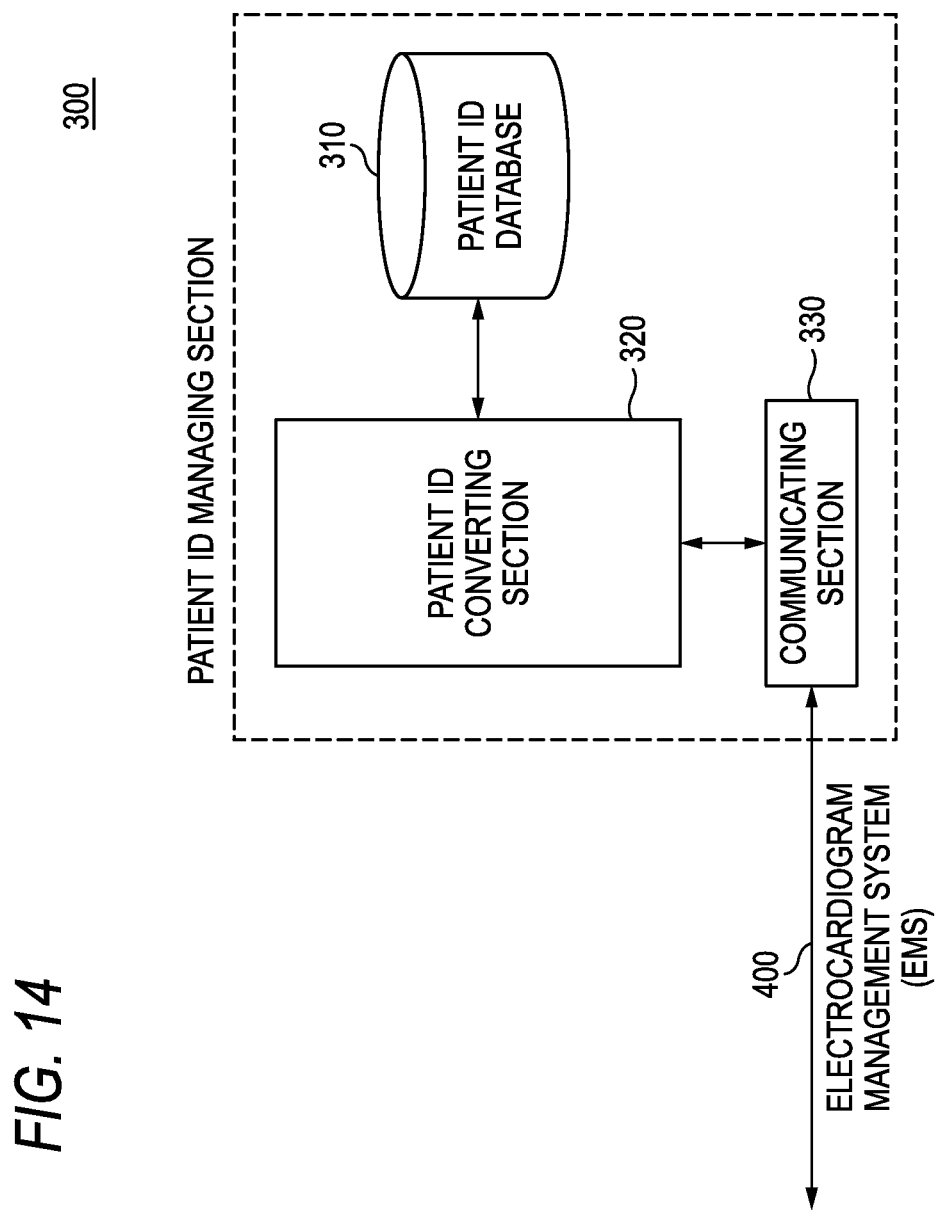
FIG. 14 is a block diagram of a patient ID managing section in the embodiment.

FIG. 14 is a block diagram of the patient ID managing section in the embodiment.

The patient ID managing section 300 includes a patient ID database 310, a patient ID converting section 320, and a communicating section 330.

The patient ID database 310 stores correspondingly the specific and individual IDs of the patient. In the case where the specific ID is "C123", the individual ID in the hospital A is "A123", and that in the hospital B is "B456", for example, "C123"-"A123" and "C123"-"B456" are stored.

The patient ID converting section 320 converts the individual ID to that in the respective hospital while referring to the specific ID of the patient.

In the case where the hospital A is to search the personal coefficient in the hospital B, for example, the patient ID database 310 is accessed while referring to the specific ID of "C123", and the individual ID of "A123" in the hospital A is converted to the individual ID of "B456" in the hospital B.

The communicating section 330 receives the specific and individual IDs of the patient transmitted from the electrocardiogram management systems 140, 240, and transmits the individual ID which is converted in the patient ID converting section 320, to the electrocardiogram management systems 140, 240.

The TWA measurement system of the embodiment has the above-described configuration.

[Operation of TWA Measurement System]

Next, the operation of the TWA measurement system of the embodiment will be described with reference to the operation flowcharts of FIGS. 15 to 23. The operation which is identical with that of the TWA measuring electrocardiograph will be briefly described.

Figure 15:
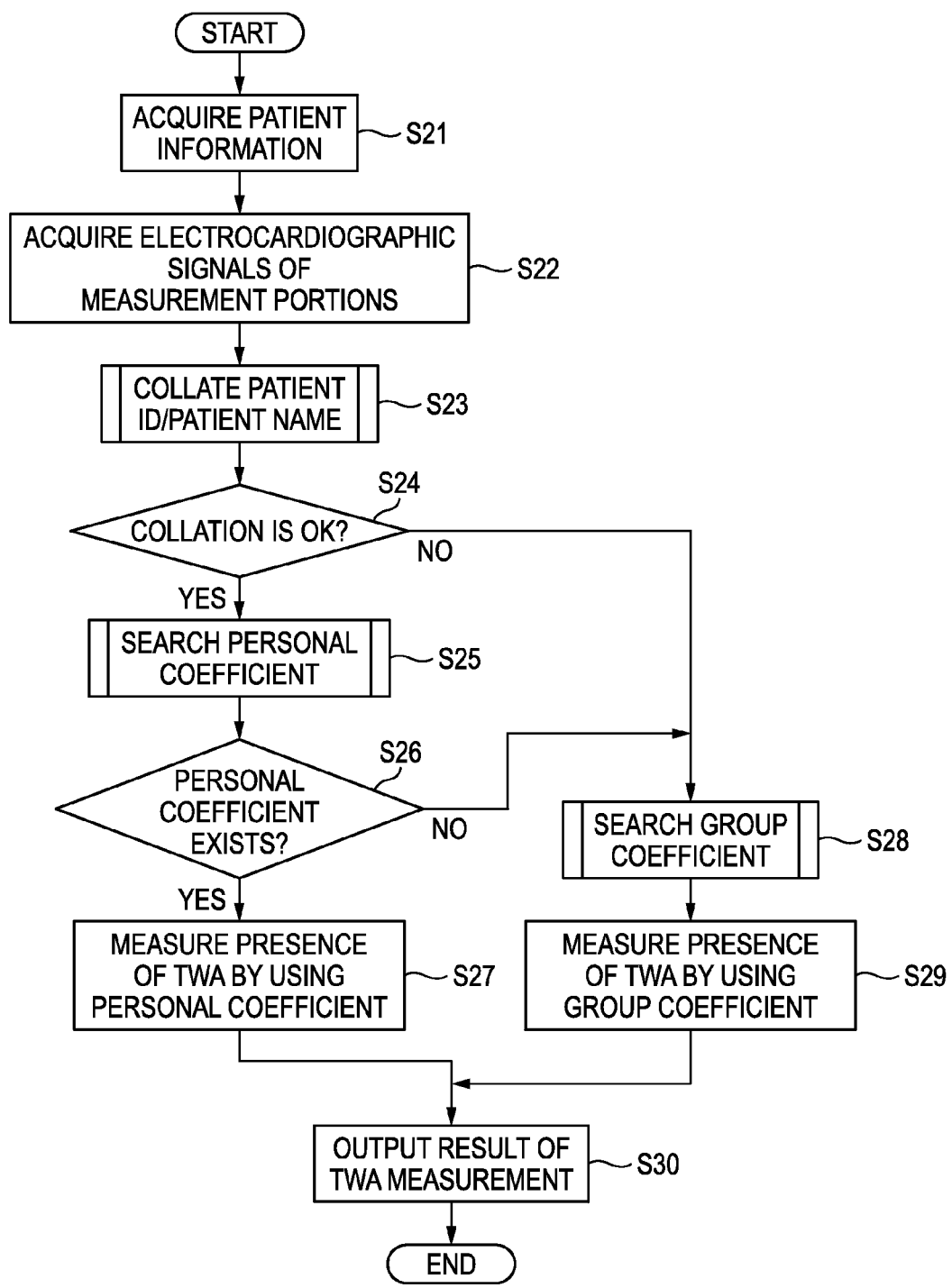
FIG. 15 is a main flowchart showing processes performed until when the TWA measuring electrocardiograph measures the presence of TWA in the TWA measurement system of the embodiment.

FIG. 15 is a main flowchart showing processes performed until when the TWA measuring electrocardiograph 110 outputs a result of the measurement of TWA of the patient. The main flowchart is performed by the electrocardiograph controlling section 117 of the TWA measuring electrocardiograph 110.

Step S21

The electrocardiograph controlling section 117 acquires the patient information supplied from the patient information inputting section 111. The patient information contains the patient ID (specific ID and individual ID), the name of the patient, the age of the patient, and the sex of the patient. The patient ID and the name of the patient are used for searching the personal coefficient of the patient, and the age and sex of the patient are used for searching the group coefficient.

Step S22

The electrocardiograph controlling section 117 acquires the electrocardiographic signals of the measurement portions from the measurement electrodes 115 which are attached to the patient.

Step S23

The electrocardiograph controlling section 117 collates the patient ID and the name of the patient with the patient ID and name of the patient which are stored in the patient information storing section 112.

Steps S24, S25

If there are a collating patient ID and a collating patient name in the patient information storing section 112, it is determined that the collation is OK (step S24: YES), and the personal coefficient stored in the personal coefficient database 113A or 143 or the personal coefficient database of the electrocardiogram management system 240 is searched.

Steps S26, S27, S30

If there is the personal coefficient of the patient in either one of the personal coefficient database 113A or 143 or the personal coefficient database of the electrocardiogram management system 240 (step S26: YES), the electrocardiograph controlling section 117 acquires the personal coefficient of the patient from the one of the personal coefficient databases 113A, 143 and the personal coefficient database of the electrocardiogram management system 240. The electrocardiograph controlling section 117 processes the electrocardiographic signals acquired by the plural measurement electrodes 115, by using the acquired personal coefficient, and measures the presence of TWA.

Step S28

By contrast, if there is not a collating patient ID and a collating patient name in the patient information storing section 112 (step S24: NO), or if there is not the personal coefficient of the patient in any one of the personal coefficient databases 113A, 143 and the personal coefficient database of the electrocardiogram management system 240 (step S26: NO), the electrocardiograph controlling section 117 searches the group coefficient stored in the transformation coefficient storing section 114. While checking the age and sex of the patient, the electrocardiograph controlling section 117 acquires a group coefficient which is optimum to the patient, from the transformation coefficient storing section 114.

Step S29

The electrocardiograph controlling section 117 processes the electrocardiographic signals detected by the plural measurement electrodes 115, by using the acquired group coefficient, and measures the presence of TWA.

Step S30

The electrocardiograph controlling section 117 outputs a result of the measurement of the presence of TWA to the displaying section 116.

Figure 16:
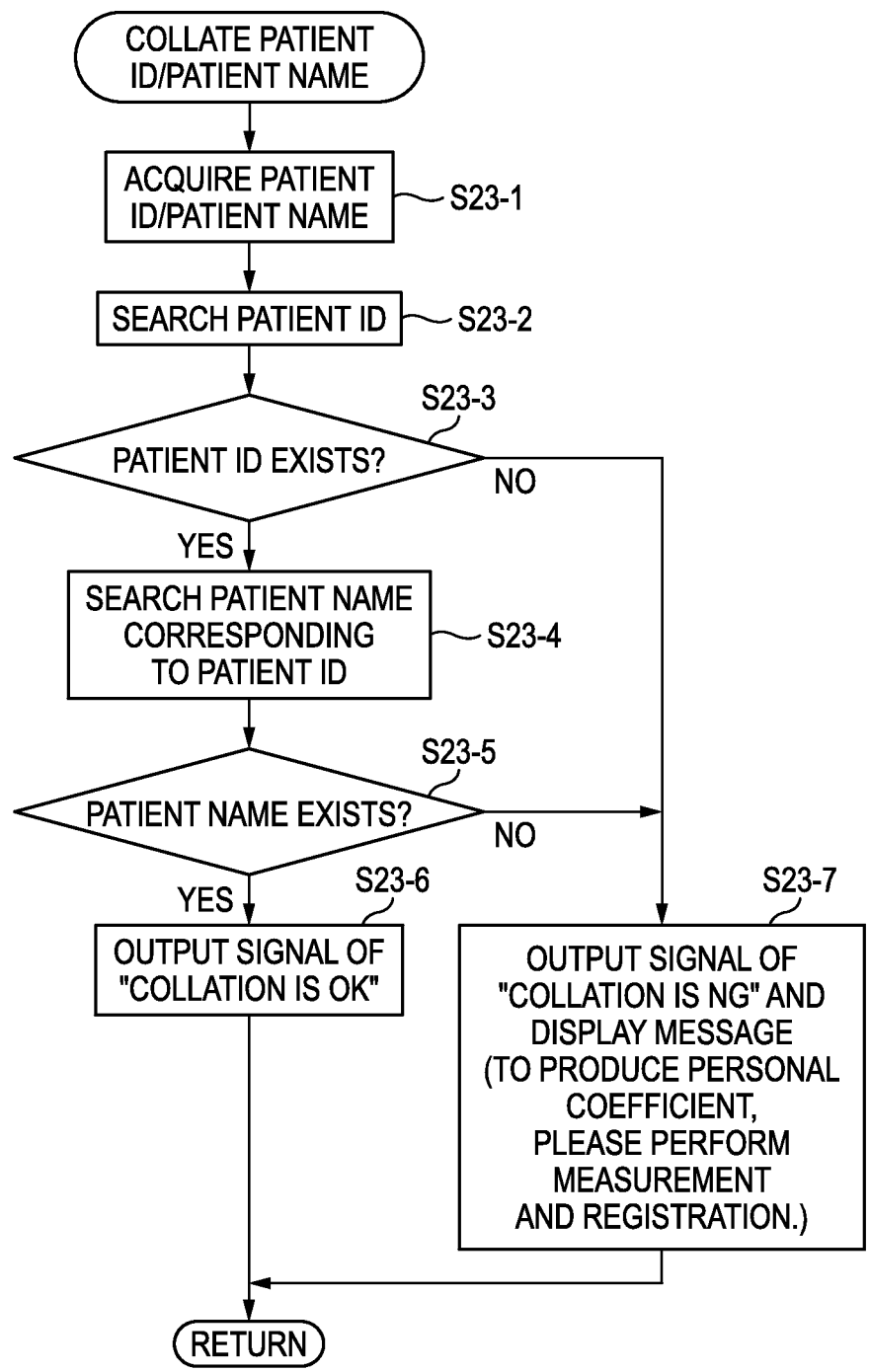
FIG. 16 is a subroutine flowchart of step S23 (COLLATE PATIENT ID/PATIENT NAME) in the main flowchart of FIG. 15.

FIG. 16 is a subroutine flowchart of step S23 (COLLATE PATIENT ID/PATIENT NAME) in the main flowchart of FIG. 15. The subroutine flowchart is performed by the electrocardiograph controlling section 117.

Step S23-1

The electrocardiograph controlling section 117 acquires the patient ID and the patient name in the patient information which is supplied from the patient information inputting section 111.

Step S23-2

The electrocardiograph controlling section 117 searches the patient ID stored in the patient information storing sections 112, 142.

Steps S23-3, S23-4

If there is the patient ID which is identical with that supplied from the patient information inputting section 111, in either one of the patient information storing section 112 or 142 (step S23-3: YES), the electrocardiograph controlling section 117 searches the patient name stored in the patient information storing section 112.

Steps S23-5, S23-6

If there is the patient name which is identical with that supplied from the patient information inputting section 111, in either one of the patient information storing section 112 or 142 (step S23-5: YES), a signal indicating that the collation is OK is output.

Step S23-3, S23-5, S23-7

If there is not a patient ID which is identical with that supplied from the patient information inputting section 111, in either one of the patient information storing section 112 or 142 (step S23-3: NO), or if there is not a patient name which is identical with that supplied from the patient information inputting section 111, in either one of the patient information storing section 112 or 142 (step S23-5: NO), a signal indicating that the collation is NG is output, and the electrocardiograph controlling section 117 causes the displaying section 116 to display a message "To produce personal coefficient, please perform measurement and registration."

Namely, if the input patient ID and patient name coincide with those which are registered in the TWA measuring electrocardiograph 110 or the electrocardiogram management system 140, it is determined that the collation is OK, and, if one of the patient ID and the patient name fails to be coincident, it is determined that the collation is NG. In the case where the collation is NG, the personal coefficient of the patient is not stored in the personal coefficient databases 113A, 143, and therefore a message for prompting acquisition of the personal coefficient is output.

Figure 17:
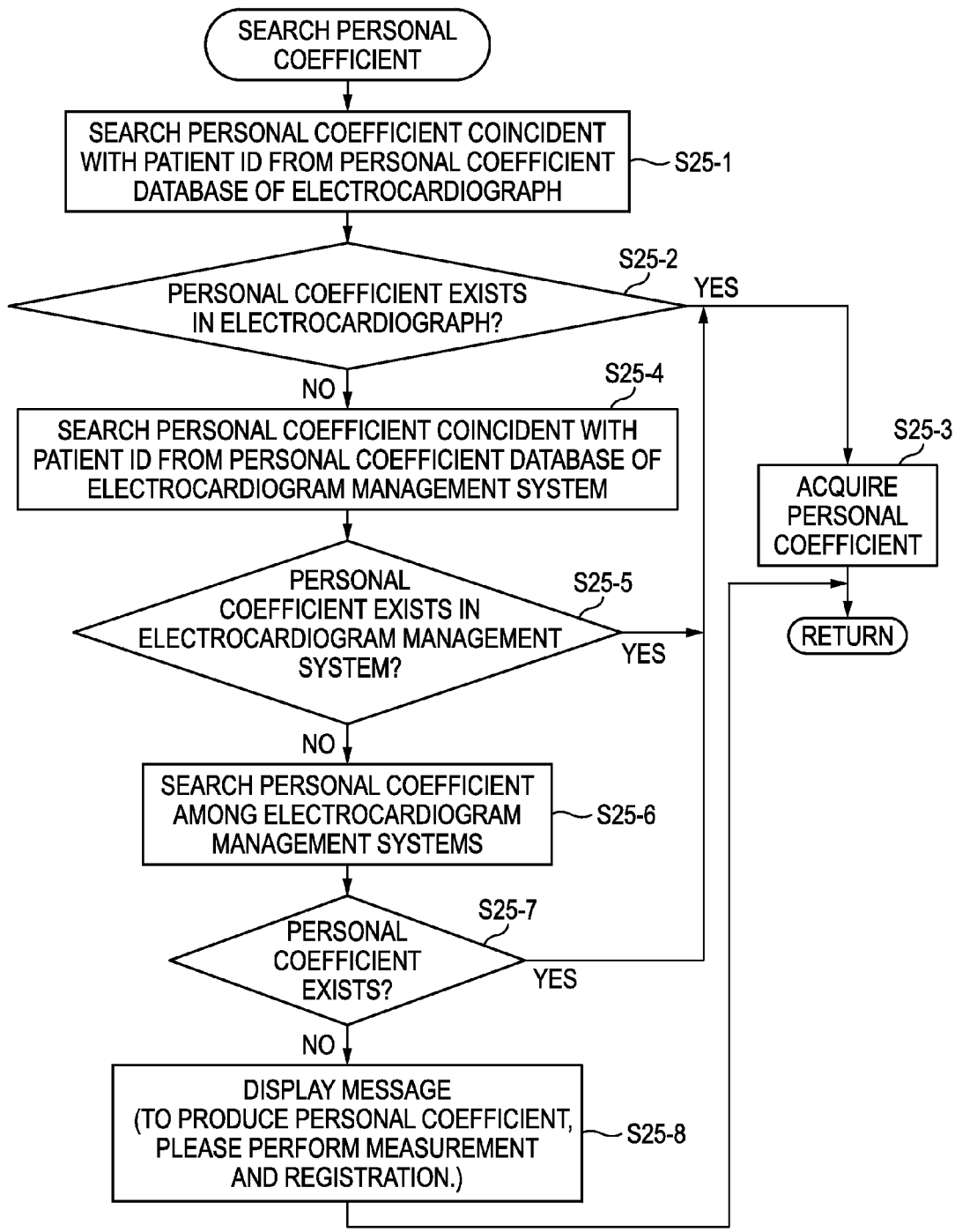
FIG. 17 is a subroutine flowchart of step S25 (SEARCH PERSONAL COEFFICIENT) in the main flowchart of FIG. 15.

FIG. 17 is a subroutine flowchart of step S25 (SEARCH PERSONAL COEFFICIENT) in the main flowchart of FIG. 15. The subroutine flowchart is performed by the electrocardiograph controlling section 117.

Step S25-1

The electrocardiograph controlling section 117 searches a personal coefficient which coincides with the patient ID, in the personal coefficient database 113A of the TWA measuring electrocardiograph 110.

Steps S25-2, S25-3

If there is the personal coefficient of the patient in the TWA measuring electrocardiograph 110 (step S25-2: YES), the electrocardiograph controlling section 117 acquires the personal coefficient from the personal coefficient database 113A.

Steps S25-2, S25-4

By contrast, if there is not the personal coefficient of the patient in the TWA measuring electrocardiograph 110 (step S25-2: NO), the electrocardiograph controlling section 117 searches the personal coefficient coincident with the patient ID in the personal coefficient database 143 of the electrocardiogram management system 140. Namely, it is searched whether the personal coefficient of the patient exists in the electrocardiogram management system 140 or not.

Steps S25-5, S25-3

If the personal coefficient of the patient exists in the electrocardiogram management system. 140 (step S25-5: YES), the electrocardiograph controlling section 117 acquires the personal coefficient from the personal coefficient database 143.

Steps S25-5, S25-6

By contrast, if the personal coefficient of the patient does not exist in the personal coefficient database 143 of the electrocardiogram management system 140 (step S25-5: NO), the electrocardiograph controlling section 117 searches the personal coefficient which is coincident with the patient ID, among the electrocardiogram management systems 140, 240. In the embodiment, the personal coefficient which is coincident with the patient ID and the type of the result of the TWA measurement is searched from the electrocardiogram management system 240. The search of the personal coefficient among the electrocardiogram management systems 140, 240 is performed by using the personal ID which is converted by the patient ID converting section 320 while using the specific ID of the patient.

Steps S25-7, S25-3

If the personal coefficient of the patient exists in the electrocardiogram management system 240 (step S25-7: YES), the electrocardiograph controlling section 117 acquires the personal coefficient from the personal coefficient database of the electrocardiogram management system 240.

Step S25-8

If the personal coefficient of the patient does not exist in the personal coefficient database of the electrocardiogram management system 240, the electrocardiograph controlling section 117 causes the displaying section 116 to display a message "To produce personal coefficient, please perform measurement and registration."

Figure 18:
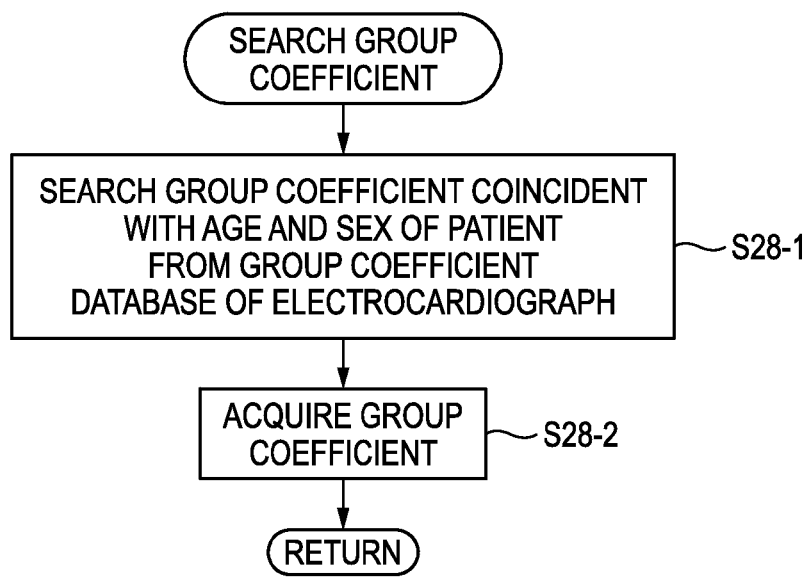
FIG. 18 is a subroutine flowchart of step S28 (SEARCH GROUP COEFFICIENT) in the main flowchart of FIG. 15.

FIG. 18 is a subroutine flowchart of step S28 (SEARCH GROUP COEFFICIENT) in the main flowchart of FIG. 15. The subroutine flowchart is performed by the electrocardiograph controlling section 117.

Step S28-1

The electrocardiograph controlling section 117 searches a group coefficient which coincides with the age and sex of the patient, in the group coefficient database 113B of the TWA measuring electrocardiograph 110. Namely, it is searched whether the group coefficient of the patient exists in the TWA measuring electrocardiograph 110 or not.

Step S28-2

The electrocardiograph controlling section 117 acquires the group coefficient from the group coefficient database 113B of the TWA measuring electrocardiograph 110.

Figure 19:
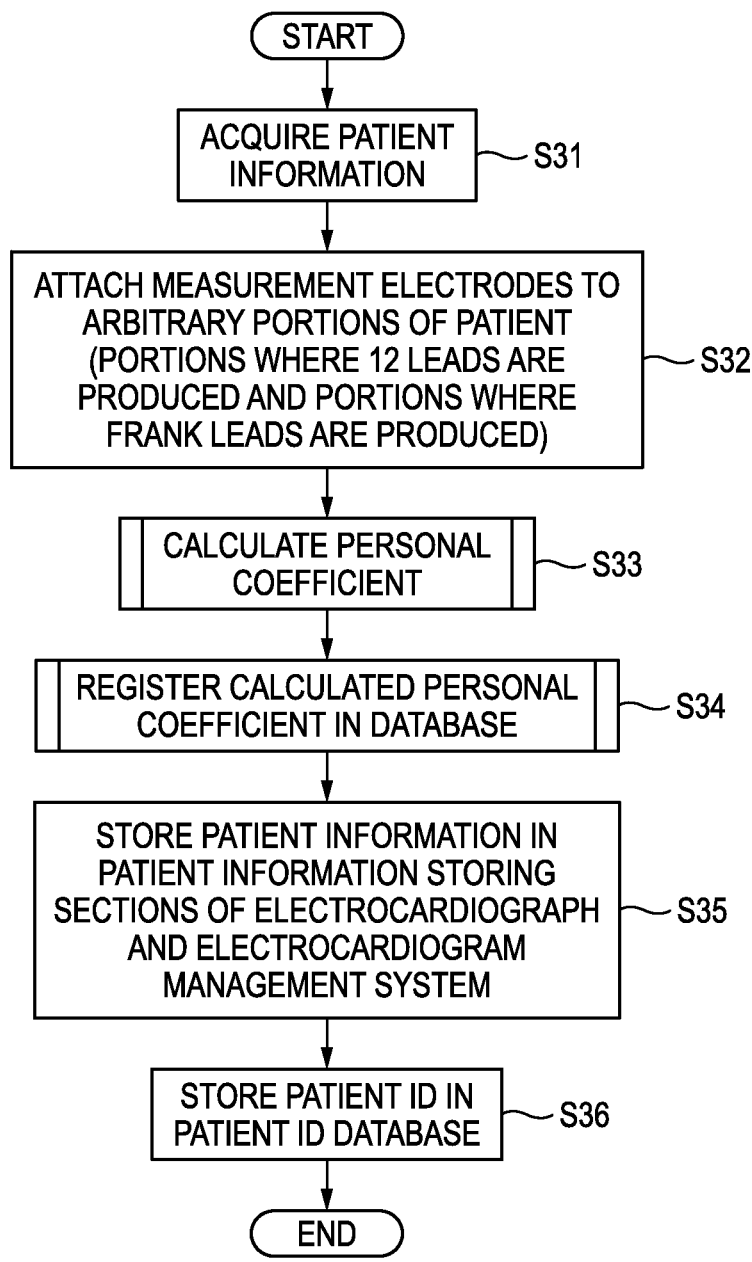
FIG. 19 is a main flowchart showing processes performed until when the personal coefficient of the patient is calculated and the calculated personal coefficient is stored in a personal coefficient database.

FIG. 19 is a main flowchart showing processes performed until when the personal coefficient of the patient is calculated and the calculated personal coefficient is stored in the personal coefficient database. The main flowchart is performed by the electrocardiograph controlling section 117.

Step S31

The electrocardiograph controlling section 117 acquires the patient information supplied from the patient information inputting section 111. The patient information contains the patient ID (specific ID and individual ID), the name of the patient, the age of the patient, and the sex of the patient. Among the patient information, the patient ID and the name of the patient are used for storing the patient coefficient of the patient in the personal coefficient database.

Step S32

The electrocardiograph controlling section 117 acquires electrocardiographic signals of arbitrary measurement portions from the measurement electrodes 115 which are attached to the patient. Specifically, for example, the measurement electrodes 115 are attached to specific portions of the patient which are determined so as to produce a 12-lead electrocardiogram (leads I and II, lead V1, lead V2, lead V3, lead V4, lead V5, and lead V6), and attached to specific portions of the patient which are determined so as to produce a Frank's vector electrocardiogram (lead I, lead E, lead C, lead A, lead H, and lead M). From the measurement electrodes 115, the electrocardiograph controlling section 117 measures leads I and II, lead V1, lead V2, lead V3, lead V4, lead V5, and lead V6 for a 12-lead electrocardiogram, and lead I, lead E, lead C, lead A, lead H, and lead M for a Frank's vector electrocardiogram.

Step S33

The electrocardiograph controlling section 117 substitutes the leads measured by means of the measurement electrodes 115, in above-described Formula 2 to calculate the personal coefficient α of the patient.

Step S34

Next, the electrocardiograph controlling section 117 stores the calculated personal coefficient in the database of the TWA measurement system, for each patient and in time series.

Step S35

The electrocardiograph controlling section 117 stores the patient information which is acquired in step S31, in the patient information storing section 112 of the TWA measuring electrocardiograph 110, and simultaneously stores the information in the patient information storing section 142 of the electrocardiogram management system 140. When the patient information is to be stored in the patient information storing section 142, the electrocardiograph controlling section 117 transmits the patient information from the communicating section 148 through the intra-hospital network 160, and the personal coefficient managing section 147 receives the patient information through the communicating section 148 of the electrocardiogram management system 140. Next, the patient information received by the personal coefficient managing section 147 is stored in the patient information storing section 142.

Step S36

Then, the electrocardiograph controlling section 117 stores the patient ID (specific ID and individual ID) of the patient information which is acquired in step S31, in the patient ID database 310 of the patient ID managing section 300. When the patient ID is to be stored in the patient ID database 310, the electrocardiograph controlling section 117 transmits the patient ID from the communicating section 148 through the intra-hospital network 160 and the connection line 400, and the patient ID converting section 320 receives the patient ID through the communicating section 330 of the patient ID managing section 300. Next, the patient ID received by the patient ID converting section 320 is stored in the patient ID database 310.

Figure 20:
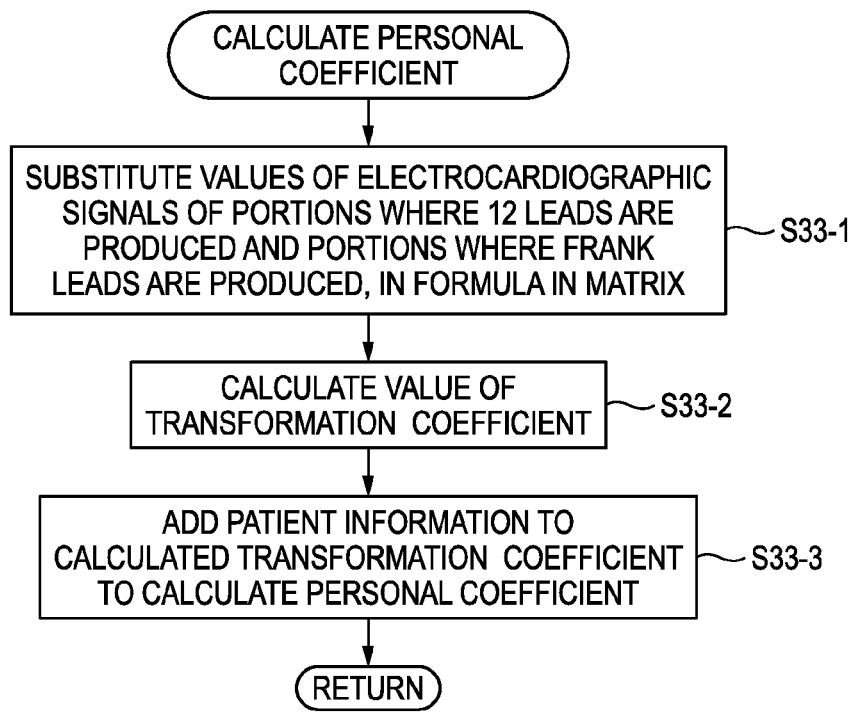
FIG. 20 is a subroutine flowchart showing a process of step S33 (CALCULATE PERSONAL COEFFICIENT) in the main flowchart of FIG. 19.

FIG. 20 is a subroutine flowchart showing a process of step S33 (CALCULATE OF PERSONAL COEFFICIENT) in the main flowchart of FIG. 19. The flowchart is performed by the electrocardiograph controlling section 117.

Step S33-1

The electrocardiograph controlling section 117 substitutes the 12-lead electrocardiogram (leads I and II, lead V1, lead V2, lead V3, lead V4, lead V5, and lead V6) and Frank's vector electrocardiogram (lead I, lead E, lead C, lead A, lead H, and lead M) which are measured by the measurement electrodes 115 attached to the patient, in above-described Formula 2.

Step S33-2

Next, the electrocardiograph controlling section 117 obtains the values of the conversion efficient from the values of leads I and II, lead V1, lead V2, lead V3, lead V4, lead V5, and lead V6, and those of lead I, lead E, lead C, lead A, lead H, and lead M.

Step S33-3

Finally, the electrocardiograph controlling section 117 adds the patient information to the obtained transformation coefficient to calculate the personal coefficient. Specifically, the patient information to be added contains the patient ID (specific ID and individual ID) and the patient name. In the above-described case, the specific ID "C123" of the patient, the individual ID "A123" of the patient, and the patient name are added as additional information, and the personal coefficient is calculated.

Figure 21:
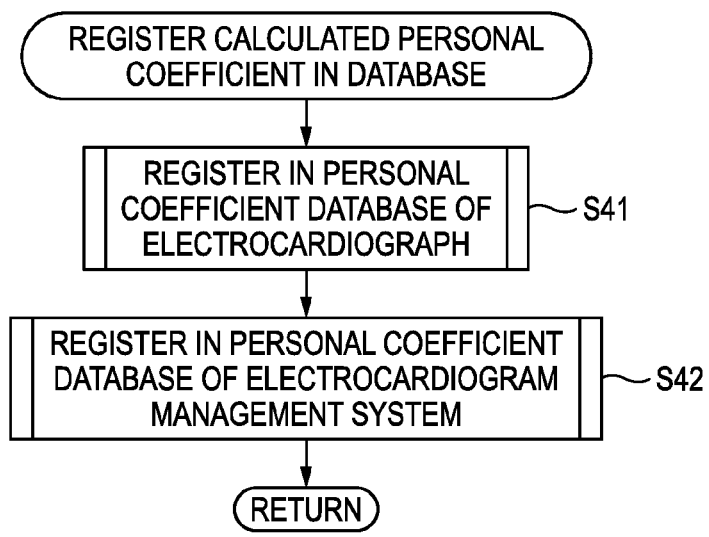
FIG. 21 is a subroutine flowchart showing a process of step S34 (REGISTER CALCULATED PERSONAL COEFFICIENT IN DATABASE) in the main flowchart of FIG. 19.

FIG. 21 is a subroutine flowchart showing a process of step S34 (REGISTER CALCULATED PERSONAL COEFFICIENT IN DATABASE) in the main flowchart of FIG. 19. The subroutine flowchart is performed by the electrocardiograph controlling section 117 and the personal coefficient managing section 147.

Step S41

First, the electrocardiograph controlling section 117 stores the calculated personal coefficient in the personal coefficient database 113A.

Step S42

Next, the personal coefficient managing section 147 stores the personal coefficient which is sent from the electrocardiograph controlling section 117, in the personal coefficient database 143. The processes of these steps are shown in detail in the subroutine flowcharts of FIGS. 22 and 23.

Figure 22:
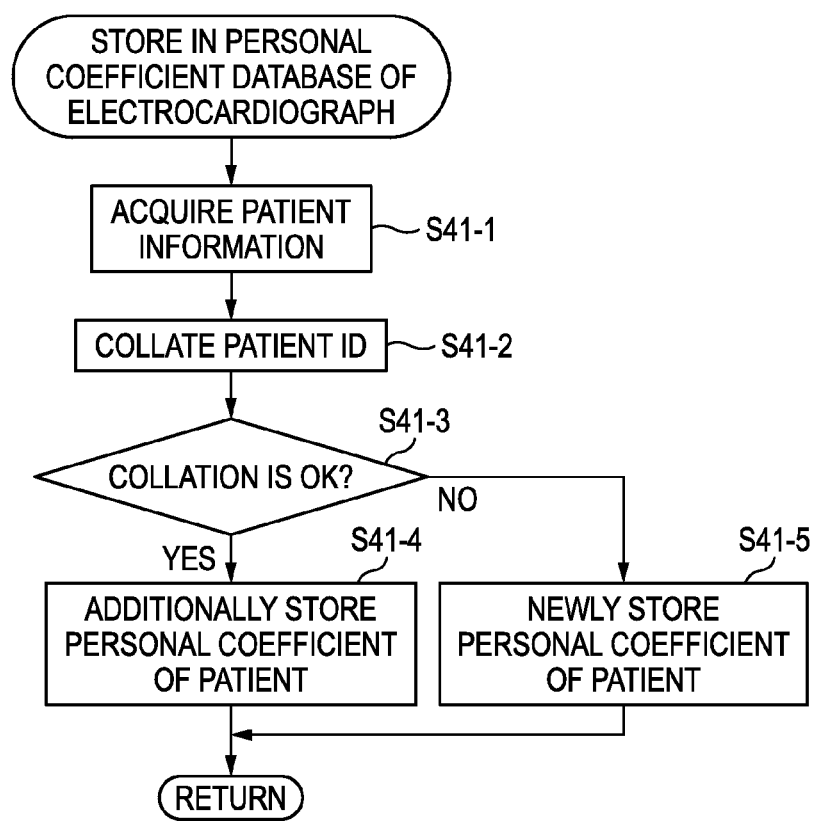
FIG. 22 is a subroutine flowchart showing a process of step S41 (STORE PERSONAL COEFFICIENT DATABASE OF TWA MEASURING ELECTROCARDIOGRAPH) in the subroutine flowchart of FIG. 21.

FIG. 22 is a subroutine flowchart showing a process of step S41 (STORE IN PERSONAL COEFFICIENT DATABASE OF TWA MEASURING ELECTROCARDIOGRAPH) in the subroutine flowchart of FIG. 21. The flowchart is performed by the electrocardiograph controlling section 117.

Step S41-1

First, the electrocardiograph controlling section 117 acquires the patient information supplied from patient information inputting section 111. The patient information contains the patient ID (specific ID and individual ID), the name of the patient, the age of the patient, and the sex of the patient.

Step S41-2

The electrocardiograph controlling section 117 collates the patient ID with that stored in the patient information storing section 112.

Steps S41-3, S41-4

If there is a collating patient ID in the patient information storing section 112, it is determined that the collation is OK (step S41-3: YES), and the electrocardiograph controlling section 117 additionally stores the personal coefficient of the patient in the personal coefficient database 113A. In the case where the same patient has already the personal coefficient, namely, the newly calculated personal coefficient is additionally stored in time series. When the personal coefficient is updated in time series, it is possible to always select the optimum coefficient of the patient, so that an accurate result of the TWA measurement can be produced.

Steps S41-3, S41-5

By contrast, if there is not a collating patient ID in the patient information storing section 112 and it is determined that the collation is NG (step S41-3: NO), the personal coefficient of the patient does not exist in the personal coefficient database 113A, and hence the electrocardiograph controlling section 117 newly stores the personal coefficient in the personal coefficient database 113A.

Figure 23:
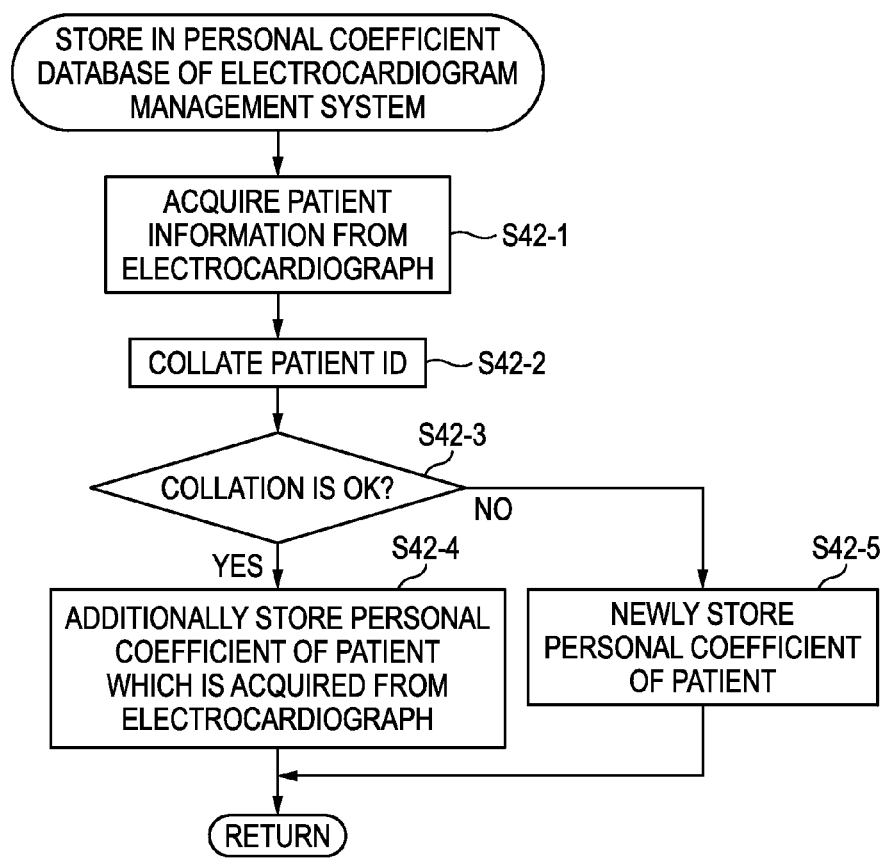
FIG. 23 is a subroutine flowchart showing a process of step S42 (STORE PERSONAL COEFFICIENT DATABASE OF ELECTROCARDIOGRAM MANAGEMENT SYSTEM) in the subroutine flowchart of FIG. 21.

FIG. 23 is a subroutine flowchart showing a process of step S42 (STORE IN PERSONAL COEFFICIENT DATABASE OF ELECTROCARDIOGRAM MANAGEMENT SYSTEM) in the subroutine flowchart of FIG. 21. The flowchart is performed by the personal coefficient managing section 147.

Step S42-1

First, the personal coefficient managing section 147 of the electrocardiogram management system 140 acquires the patient information from the TWA measuring electrocardiograph 110. The patient information contains the patient ID (specific ID and individual ID), the name of the patient, the age of the patient, and the sex of the patient.

Step S42-2

The personal coefficient managing section 147 collates the patient ID with that stored in the patient information storing section 142.

Steps S42-3, S42-4

If there is a collating patient ID in the patient information storing section 142, it is determined that the collation is OK (step S42-3: YES), the personal coefficient managing section 147 additionally stores the personal coefficient of the patient in the personal coefficient database 143. In the case where the same patient has already the personal coefficient, namely, the newly calculated personal coefficient is additionally stored in time series.

Steps S42-3, S42-5

By contrast, if there is not a collating patient ID in the patient information storing section 142 and it is determined that the collation is NG (step S42-3: NO), the personal coefficient of the patient does not exist in the personal coefficient database 143, and hence the personal coefficient managing section 147 newly stores the personal coefficient in the personal coefficient database 143.

As described above, according to the TWA measuring electrocardiograph, TWA measuring method, and TWA measurement system of the embodiment, the use of a transformation coefficient enables a Frank's vector electrocardiogram to be derived from a 12-lead electrocardiogram. Therefore, the measuring person may attach the measurement electrodes to the same positions as those in the case where a 12-lead electrocardiogram is to be acquired. Since the presence of TWA can be measured from the derived 12-lead electrocardiogram, the presence of TWA can be measured in the same manner as the case where a 12-lead electrocardiogram is to be acquired. Moreover, the personal coefficient specific to the patient is used for measuring the presence of TWA of the patient, and therefore an optimum result of the TWA measurement can be acquired, so that the measurement accuracy can be improved.

The embodiment in which the personal coefficient is stored for each patient and in time series has been described. In the case where the storage capacity of the TWA measuring electrocardiograph is small, the personal coefficient may not be stored in time series, but only the latest personal coefficient may be updatingly stored. The embodiment is configured so that, in the case where the personal coefficient of a specific patient exists, even when the personal coefficient was produced, for example, two or three years ago, the personal coefficient can be used. In order that the presence of TWA of the patient can be examined highly accurately, however, it is preferable that a result of the TWA measurement is produced by using a personal coefficient which is acquired at a timing as close as possible to the present timing. Alternatively, therefore, an available period (for example, one year from acquisition) of a personal coefficient may be set. In the case where the available period is expired, acquisition of the personal coefficient may be prompted in a similar manner as the case where the personal coefficient does not exist, and a process such as that shown in the flowchart of FIG. 20 may be performed.

In the embodiment, the conversion of the individual ID is performed in order to search and acquire the personal coefficient between hospitals. The conversion of the individual ID is performed in accordance with the specific ID. Various techniques for ID conversion are known. The technique for ID conversion is not limited to that exemplified in the embodiment, and any one of the various known techniques may be employed. For example, an open software application called OpenPIXPDQ is known as a software application for ID conversion between hospitals. The conversion of the ID may be performed by using such an open software application.

The invention is not limited to the above-described embodiment. The technical scope of the invention includes the above-described embodiment and also other embodiments which may be modified by those skilled in the art.

According to an aspect of the invention, the electrocardiograph controlling section produces a scalar electrocardiogram from the electrocardiographic signals of the measurement electrodes. The electrocardiograph controlling section can produce the scalar electrocardiogram by using any one of various measuring methods. The number and positions of the measurement electrodes to be attached to the subject are different depending on the measuring method which is used for acquiring the scalar electrocardiogram (for example, a usual standard 12-lead electrocardiogram, a derived 12-lead electrocardiogram, an exercise electrocardiogram, a Holter electrocardiogram, or a monitoring electrocardiogram). The electrocardiograph controlling section derives the Frank's vector electrocardiogram by multiplying the scalar electrocardiogram which is produced by using anyone of various measuring methods, with the transformation coefficient stored in the transformation coefficient storing section. The TWA measuring section measures the presence of TWA based on the waveform of the Frank's vector electrocardiogram which is derived by the electrocardiograph controlling section.

According to an aspect of the invention, the TWA measuring electrocardiograph includes: the measurement electrodes which are to be attached to the subject in order to produce a scalar electrocardiogram; a transformation coefficient storing section which stores a transformation coefficient for deriving a Frank's vector electrocardiogram; an electrocardiograph controlling section which produces the scalar electrocardiogram from electrocardiographic signals of the measurement electrodes, and which derives the Frank's vector electrocardiogram from the scalar electrocardiogram by using the transformation coefficient; and a TWA measuring section which measures a presence of TWA based on the derived Frank's vector electrocardiogram. The transformation coefficient storing section includes: a personal coefficient database which stores a personal coefficient that is acquired from the subject and that is specific to the subject, as the transformation coefficient; and a group coefficient database which, as the transformation coefficient, stores a group coefficient that is the average of a plurality of transformation coefficients acquired from an unspecified number of persons of a statistically effective population in order to derive the Frank's vector electrocardiogram of the subject.

According to an aspect of the invention, similarly with the transformation coefficient storing section provided in the TWA measuring electrocardiograph, also the electrocardiogram management system includes a personal coefficient database. In the case where the personal coefficient that is specific to the subject does not exist in the TWA measuring electrocardiograph, therefore, the TWA measuring electrocardiograph measures the presence of TWA by using a personal coefficient provided from the electrocardiogram management system, as the transformation coefficient.

According to an aspect of the invention, a Frank's vector electrocardiogram can be derived from a scalar electrocardiogram, and hence the measuring person can attach the measurement electrodes to the positions identical with those in the case where a scalar electrocardiogram is to be acquired. Since the presence of TWA can be measured from the derived Frank's vector electrocardiogram, it is possible to measure the presence of TWA in the same manner as the case where the scalar electrocardiogram is acquired.

What is claimed is:

1. A T-wave alternans (TWA) measuring electrocardiograph comprising:
    a transformation coefficient storing section configured to store a transformation coefficient for deriving a Frank's vector electrocardiogram;
    an electrocardiograph controlling section configured to produce a scalar electrocardiogram from electrocardiographic signals of measurement electrodes adapted to be attached to a subject, and configured to derive the Frank's vector electrocardiogram from the scalar electrocardiogram by using the transformation coefficient; and
    a TWA measuring section configured to measure a presence of TWA based on the derived Frank's vector electrocardiogram,
    wherein the transformation coefficient storing section comprises:
        a personal coefficient database configured to store a personal coefficient that is acquired from the subject and that is specific to the subject, as the transformation coefficient; and
        a group coefficient database configured to store, as the transformation coefficient, a group coefficient that is an average of a plurality of transformation coefficients acquired from an unspecified number of persons of a statistically effective population.

2. The TWA measuring electrocardiograph according to claim 1, wherein when the personal coefficient database stores the personal coefficient, the electrocardiograph controlling section derives the Frank's vector electrocardiogram by using the personal coefficient as the transformation coefficient, and when the personal coefficient database does not store the personal coefficient, the electrocardiograph controlling section derives the Frank's vector electrocardiogram by using the group coefficient stored in the group coefficient database as the transformation coefficient.

3. The TWA measuring electrocardiograph according to claim 2, wherein when the personal coefficient database does not store the personal coefficient, the electrocardiograph controlling section causes a displaying section to display a message for prompting acquisition of the personal coefficient.

4. The TWA measuring electrocardiograph according to claim 2, wherein the electrocardiograph controlling section calculates the personal coefficient from the electrocardiographic signals of the measurement electrodes, and stores the calculated personal coefficient in the personal coefficient database.

5. The TWA measuring electrocardiograph according to claim 1, wherein the TWA measuring section measures the presence of TWA based on a waveform of a vector magnitude which is obtained from the Frank's vector electrocardiogram.

6. The TWA measuring electrocardiograph according to claim 5, wherein the TWA measuring section selects a waveform which contributes to measurement of the presence of TWA, from the waveform of the vector magnitude, and measures the presence of TWA from the selected waveform.

7. The TWA measuring electrocardiograph according to claim 6, wherein in the selected waveform which contributes to the measurement of the presence of TWA, the TWA measuring section detects an outlier, which adversely affects the measurement of the presence of TWA, in an odd beat or an even beat, and corrects a beat including the detected outlier.

8. A TWA measurement system comprising:
the TWA measuring electrocardiograph according to claim 1; and
an electrocardiogram management system configured to manage information related to the Frank's vector electrocardiogram derived by the TWA measuring electrocardiograph, and including a personal coefficient database configured to provide a personal coefficient as the transformation coefficient to the TWA measuring electrocardiograph.

9. The TWA measurement system according to claim 8, wherein the electrocardiograph controlling section of the TWA measuring electrocardiograph acquires the personal coefficient, from the personal coefficient database of the TWA measuring electrocardiograph or the personal coefficient database of the electrocardiogram management system.

10. A T-wave alternans (TWA) measuring method comprising:
attaching measurement electrodes to a subject;
producing a scalar electrocardiogram from electrocardiographic signals of the measurement electrodes;
acquiring a transformation coefficient for deriving a Frank's vector electrocardiogram;
deriving the Frank's vector electrocardiogram from the scalar electrocardiogram by using the transformation coefficient; and
measuring a presence of TWA from the derived Frank's vector electrocardiogram,
wherein the acquiring comprises:
determining whether a personal coefficient that is acquired from the subject and that is specific to the subject exists in a coefficient database; and
obtaining the personal coefficient as the transformation coefficient in response to determining that the personal coefficient exists in the coefficient database, and obtaining a group coefficient as the transformation coefficient from the coefficient database, the group coefficient being an average of a plurality of transformation coefficients acquired from an unspecified number of persons of a statistically effective population, in response to determining that the personal coefficient does not exist in the coefficient database.

11. The TWA measuring method according to claim 10, wherein, in the process of measuring the presence of TWA, the presence of TWA is measured based on a waveform of a vector magnitude which is obtained from the Frank's vector electrocardiogram.

12. The TWA measuring method according to claim 11, wherein, in the process of measuring the presence of TWA, a waveform which contributes to measurement of the presence of TWA is selected from the waveform of the vector magnitude, and the presence of TWA is measured from the selected waveform.

13. The TWA measuring method according to claim 12, wherein, in the process of measuring the presence of TWA, in the selected waveform which contributes to the measurement of the presence of TWA, an outlier, which adversely affects the measurement of the presence of TWA, is detected in an odd beat or an even beat, and an beat including the detected outlier is corrected.

* * * * *